(12) United States Patent
Bishop et al.

(10) Patent No.: US 6,671,541 B2
(45) Date of Patent: Dec. 30, 2003

(54) CARDIOVASCULAR IMAGING AND FUNCTIONAL ANALYSIS SYSTEM

(75) Inventors: Harry Bishop, Bridgeport, WV (US); Stanislaw Majewski, Yorktown, VA (US); Marc M. Umeno, Cleveland Heights, OH (US)

(73) Assignee: NeoMed Technologies, Inc., Cleveland, OH (US)

( * ) Notice: Subject to any disclaimer, the term of this patent is extended or adjusted under 35 U.S.C. 154(b) by 231 days.

(21) Appl. No.: 09/726,358

(22) Filed: Dec. 1, 2000

(65) Prior Publication Data

US 2002/0188197 A1 Dec. 12, 2002

(51) Int. Cl.[7] ................................................. A61B 6/00
(52) U.S. Cl. ..................... 600/436; 600/431; 250/363.1; 250/370.09
(58) Field of Search ................................. 600/436, 431, 600/407; 250/367, 370, 366

(56) References Cited

U.S. PATENT DOCUMENTS

| | | | |
|---|---|---|---|
| 4,221,967 A | * 9/1980 | Wang et al. | 250/214 VT |
| 4,458,688 A | * 7/1984 | Von Behren | 430/281.1 |
| H12 H | * 1/1986 | Bennett et al. | 250/363.04 |
| 5,274,549 A | * 12/1993 | Almasi | 382/128 |
| 5,420,429 A | * 5/1995 | Eberhard et al. | 250/367 |
| 5,608,221 A | * 3/1997 | Bertelsen et al. | 250/363.03 |
| 5,722,405 A | * 3/1998 | Goldberg | 600/407 |
| 5,811,813 A | * 9/1998 | Maor | 250/363.04 |
| 5,847,398 A | * 12/1998 | Shahar et al. | 250/370.09 |
| 5,871,013 A | * 2/1999 | Wainer et al. | 250/363.04 |
| 6,180,946 B1 | * 1/2001 | Ebstein | 250/370.11 |
| 6,362,479 B1 | * 3/2002 | Andreaco et al. | 250/363.01 |
| 6,377,838 B1 | * 4/2002 | Iwanczyk et al. | 600/425 |
| 6,392,236 B1 | * 5/2002 | Maekawa et al. | 250/369 |
| 6,420,711 B2 | * 7/2002 | Tumer | 250/370.09 |
| 2002/0011571 A1 | * 1/2002 | Lin et al. | 250/366 |

* cited by examiner

Primary Examiner—Marvin M. Lateef
Assistant Examiner—Barry Pass
(74) Attorney, Agent, or Firm—Paul V. Keller

(57) ABSTRACT

A cardiovascular imaging and functional analysis system and method is disclosed, wherein a dedicated fast, sensitive, compact and economical imaging gamma camera system that is especially suited for heart imaging and functional analysis is employed. The cardiovascular imaging and functional analysis system of the present invention can be used as a dedicated nuclear cardiology small field of view imaging camera. The disclosed cardiovascular imaging system and method has the advantages of being able to image physiology, while offering an inexpensive and portable hardware, unlike MRI, CT, and echocardiography systems.

The cardiovascular imaging system of the invention employs a basic modular design suitable for cardiac imaging with one of several radionucleide tracers. The detector can be positioned in close proximity to the chest and heart from several different projections, making it possible rapidly to accumulate data for first-pass analysis, positron imaging, quantitative stress perfusion, and multi-gated equilibrium pooled blood (MUGA) tests..

In a preferred embodiment, the Cardiovascular Non-Invasive Screening Probe system can perform a novel diagnostic screening test for potential victims of coronary artery disease. The system provides a rapid, inexpensive preliminary indication of coronary occlusive disease by measuring the activity of emitted particles from an injected bolus of radioactive tracer. Ratios of this activity with the time progression of the injected bolus of radioactive tracer are used to perform diagnosis of the coronary patency (artery disease).

34 Claims, 18 Drawing Sheets

BOTTOM VIEW

SIDE VIEW

SIDE VIEW

BOTTOM VIEW

CARDIOVASCULAR IMAGING AND FUNCTIONAL ANALYSIS SYSTEM

BACKGROUND OF THE INVENTION

1. Field of the Invention

The present invention relates to medical diagnostic and screening apparatus and methods. Particularly, the present invention relates to non-invasive medical diagnostic and screening systems. Still more particularly, the present invention relates to non-invasive imaging and functional analysis systems for evaluating cardiac and cardiovascular health.

2. Related Art

Cardiac imaging and functional analysis is the largest single nuclear medical imaging application and represents the area of greatest unmet need in the prior art. This need is exemplified by the fact that historically, for 30%–50% of those stricken with coronary occlusive (artery) disease, the first symptom of the disease is death. This outcome has motivated considerable interest in developing diagnostic methods and apparatus to detect the condition of coronary occlusive disease prior to the onset of fatal symptoms, and further to assist in the development and implementation of preventive measures.

First-Pass RNA

First-Pass Radionucleide Angiography (RNA) provides the clinician with patient information for improved patient management that is either difficult and/or costly to obtain using other technologies. The First-Pass RNA can provide unique qualitative and quantitative information about cardiac function such as regional ventricular wall motion just at the peak of maximum exercise stress, left and right ventricular ejection fraction, regional contractivity, and left to right shunt quantitation. Concurrently, improvements in software analysis of the diagnostic tests are being developed and implemented on a regular basis. However, medical instrument improvements have not kept pace with detector hardware enhancements such as pixellated scintillation crystals, and position-sensitive photomultipliers. Presently, the nuclear medicine health care sector can perform a first—pass RNA diagnostic protocol using the commercially available dedicated cardiac imager multicrystal scanner model SIM400 from Picker International or a single crystal Anger gamma camera. The single crystal Anger camera has numerous disadvantages when used for first-pass RNA related to its low count rate capability including pulse-pileup and low count density. A low-count density image limits the ability to define changes in wall motion. Improvements in defining wall motion are attained using the multicrystal high rate camera. Other factors influencing the image quality are the intrinsic system resolution, count density, and the target-to-nontarget ratio.

The SIM400 scanner uses a 2.54 cm thick Na1(Tl) crystal divided into 400 detector elements in a 20×20 matrix. Surrounding each detector element is reflective material. Every second row is partially cut through the crystal to create a scintillation bridge between two adjacent elements. The scintillation light is detected by 115¾" diameter bialkali tubes and each photomultiplier tube (PMT) detects scintillation from two optically decoupled detector elements. Variations in pulse output from adjacent PMTs viewing the doublet detector element provides the photon spatial information. This scenario provides for improved count rate capability but limits spatial resolution.

In practice, clinical interpretations of the SIM400 scanner treadmill stress acquisitions are more difficult to analyze. Patient motion during peak stress acquisition can cause image artifacts that can trigger an incorrect diagnosis. To counteract this problem Picker International uses an Am-241 source placed on the patients' chest. Dual energy windows are utilized during treadmill stress acquisitions and the Am-241 energy window is used to correct for patient motion. Unfortunately, this method only corrects for up/down/side planar motion, i.e., motion in a plane, and motion in any direction outside the defined plane is uncorrected. If the patient rotates along the z-axis, the planar patient correction can magnify image artifacts. The solution of using an array of fast compact photomultiplier tubes (PMTs) to obtain compact application-specific highrate gamma cameras is described in literature. However, the prior art instruments were slow, designed primarily for relatively low rate (up to 5 kHz) breast imagers. The array concept was conceived and first tested in a small laboratory prototype by Dr. Roberto Pani and his group in University "La Sapienza" in Rome, Italy. At the time of this application, there are three companies in US that are developing products based on this mature and reliable concept: Gamma Medica Instruments (www.gammamedica.com), Dilon Technologies (www.dilon.com), and PEM Technologies, Bethesda, Md. Initially, imaging of breast cancers was emphasized, taking advantage of the small size of the cameras that allows flexibility in positioning the detector for better localization and visualization of breast lesions. One company, Digirad (www.digirad.com), produces heart imagers based on not yet technically mature and expensive solid state technology (CsI(T1) scintillator and PIN diode arrays). The only high count-rate dedicated heart imager (developed by Proportional Technologies, Inc. Houston) is based on a high pressure wire chamber concept and therefore has its energy range practically limited to less than 100 keV. Also, its rate capability is in fact limited by the physical nature of radiation interaction with a gas detector medium in a two-step process.

Positron Imaging

At the present time, essentially all nuclear cardiac imaging is limited to single-photon tomography for myocardial perfusion determination. This examination is more accurately performed by positron imaging. Prior to cardiac revascularization there is a great need to determine the viability of hypoperfused myocardium. This is accurately determined only by positron imaging. The capability to image the annihilation radiation from positron tracers will greatly increase the usefulness of a cardiac gamma camera. From the list of the presently available detection technologies of: crystal scintillators with photomultipliers, scintillators with PIN photodiodes, scintillators with avalanche photodiodes (APDS), gas filled detectors, Cadmium Zinc Telluride (CdZnTe) and other solid state detection materials, only the first solution is viable at this time from the technical and economical point of view and can be used for positron imaging as well as single gamma imaging. The detection efficiency and excellent signal to noise ratio, good energy resolution, and above all the unmatched speed of operation of fast scintillator/compact photomultiplier combination makes it the solution of choice for a combined single gamma/positron imager. The easily implemented modular structure with segmented fast readout adds to the list of main advantages of this preferred solution. However, it is possible that further development of some of the other detection technologies can lead to another option for the screening and diagnostic instruments and procedures described in this disclosure.

Coronary Artery Disease (CAD) Screening

There are two screening strategies to reduce morbidity and mortality from CAD. The first involves screening for modifiable cardiac risk factors, such as hypertension, elevated serum cholesterol, cigarette smoking, physical inactivity, and diet. The second strategy is early detection of asymptomatic CAD. The principal tests for detecting asymptomatic CAD include resting and exercise ECGs, which can provide evidence of previous silent myocardial infarctions and silent or inducible myocardial ischemia. Another principal test is computed tomography (CT) calcification scoring, which can provide visual evidence of plaques in the coronary arteries. Thallium201 scintigraphy, exercise echocardiography, and ambulatory ECG (Holter monitoring) are less commonly used for screening purposes. Neither of these strategies has produced a solution to the high incidence of previously asymptomatic CAD deaths.

Need for Solutions

In summary, nuclear cardiology equipment has evolved in recent years in the direction of more complex and expensive devices. However, the need for such high-performance imaging technology remains acute. Accordingly, there exists a need for a dedicated nuclear cardiac imaging equipment that is simpler in design, manufacture and use than the prior art. A need also exists for such simple, low cost equipment that can perform first pass imaging, positron imaging, quantitative myocardial perfusion measurements, multi-gated equilibrium pooled blood (MUGA) imaging and coronary transit-time screening. Further, there is a need for portability of such a device.

Naturally, several embodiments of such an invention could solve many or all of the unmet needs of the prior art, and will simultaneously implement new procedures in nuclear medicine that are not currently utilized. Emergency room cardiac triage and bedside patient monitoring are examples of applications that can utilize portable, compact imaging detectors such that the imaging equipment can be taken to the patient vs. the patient taken to the equipment. The portability of the camera also lends itself for imaging in other situations where a patient movement is undesirable. For instance, patients with kidney transplants require frequent evaluation of blood flow and function using renal tracers. Determination of brain viability is also best done at bedside. The risk of transporting these patients to nuclear medicine department inhibits currently optimal utilization of these diagnostic techniques.

Related teachings and prior art include the following:

[1] Dr. Roberto Pani's papers on multi-PSPMT imagers:
  a) Single Photon Emission Imaging by Position Sensitive PMT. Pani R., Pellegrini R., Soluri A., De Vincentis G., Scafé R., Pergola A, Nucl. Instr. & Meth. 1998. A 409:524–528.
  b) Multi PSPMT Scintillating camera. Pani R., Soluri A., Scafé R.,Pergola A., Pellegrini R., De Vincentis G.,G. Trotta, Scopinaro F. 1997 IEEE Nuclear Science Simposium, Conference Record vol.2 pg. 1068–1072, Nov. 9–15,1997 Albuquerque, N. Mex. USA.
  c) Multi PSPMT Scintillating camera. Pani R., Soluri A., Pergola A., Pellegrini R., Scafé R., De Vincentis G., Scopinaro F. IEEE Trans. on Nuclear Science 46 N.3; 702–708, 1999.

[2] New Developments in Portable Gamma Cameras. Joyce Ward, ADVANCE for Radiologic Science Professionals, page 16–17, Aug. 3, 1998.

[3] U.S. Pat. No. 6,091,070: Semiconductor Gamma-Ray Camera and Medical Imaging System, Lingren C. L. et al., Jul. 18, 2000.

[4] U.S. Pat. No. 4,458,688: Method and Apparatus for Cardiac Nuclear Imaging, Von Behren P. L., Jul. 10, 1984.

[5] U.S. Pat. No. 4,999,501: High speed multiwire photon camera, Lacy J. L., Mar. 12, 1991.

[6] U.S. Pat. No. 5,753,917: Dual crystal scintillation camera, Engdahl J. C. May 19, 1998.

[7] U.S. Pat. No. 5,431,161: Method and apparatus for information acquistion, processing, and display within a medical camera system, Ryals Carl J. et al., Jul. 11, 1995.

[8] U.S. Pat. No. 5,377,681: Method of diagnosing impaired blood flow, Drane Walter E., Jan. 3, 1995.

[9] U.S. Pat. No. 5,249,124: Multi-isotope imaging using energy-weighted acquisition for, e.g., myocardial perfusion studies, DeVito; Raymond P., Sep. 28, 1993.

[10] U.S. Pat. No. 5,199,438: Measurement of cardiac performance, Pearlman Andrew L. Apr. 6, 1993.

[11] Scintillation products from Saint Gobain Crystals and Detectors (formerly: Bicron Corporation), Newbury, Ohio.

[12] Compact and Flat Panel photomulltipliers from Hamamatsu Corporation, Bridgewater, N.J.

[13] Model 85001 000 photomultiplier from Burle Industries, Inc, Lancaster, Pa.

SUMMARY OF THE INVENTION

To overcome the above-mentioned shortcomings of the prior art, a dedicated cardiovascular imaging and functional analysis system is disclosed.

The present invention has several unique technical features, including pixellated scintillation detectors, fast compact photomultipliers, matching high efficiency light guide system, very fast readout and data processing systems, and novel imaging and functional analysis algorithms. In a first embodiment of the dedicated cardiovascular imaging and functional analysis system, the cardiovascular imaging system of the present invention comprises a dedicated fast, sensitive, compact and economical imaging gamma camera system that is especially suited for heart imaging. The cardiovascular imaging system of the present invention can be used as a dedicated nuclear cardiology small field of view imaging camera. Embodiments of the present invention for dedicated nuclear cardiographic imaging will compete with magnetic resonance imaging (MRI), computed tomography (CT), and echocardiography; all of which are slowly adopting nuclear cardiology practice. The present invention has the advantages of being able to image physiology, yet also has the potential to be inexpensive and portable, unlike current nuclear medical, MRI, CT, and echocardiography systems.

The cardiovascular imaging system of the present invention employs a basic modular design that can be used in the compact camera system suitable for cardiac imaging with one or more radionucleide tracers. The detector can be positioned in close proximity to the chest and heart from several different projections, making it possible rapidly to accumulate data for first-pass analysis and ejection fraction of both right and left ventricles. The portability of the instrument would also make it very desirable for imaging in the cramped quarters of intensive care units in the cases when it would be not practical to transport the patients to the nuclear cardiology department. Furthermore, preferred embodiments of the present invention include at least a second camera head, routinely placed at approximately a right angle to the first camera head to provide additional out-of-plane views. The additional camera angle permits the system to account for patient motion in all planes, and eliminating artifacts caused by such patient motion. This is especially useful in traditional stress testing.

In a second preferred embodiment, the Cardiovascular Non-Invasive Screening Probe system is to perform a novel diagnostic screening test for potential victims of coronary occlusive disease. This system will provide a rapid, inexpensive preliminary indication of coronary occlusive disease by measuring the activity of emitted particles from an injected bolus of radioactive tracer. Ratios of this activity with the time progression of the injected bolus of radioactive tracer will be used to perform diagnosis of the coronary patency (artery disease).

In this preferred embodiment, this screening test detects coronary insufficiency. Most resting patients with occlusive disease of proximal coronary arteries maintain normal coronary (volume) blood flow. During this period, all standard measures of cardiac hemodynamic functions, i.e., those tests used by today's cardiologists, are not sensitive to a coronary insufficiency. That is why traditional "stress" tests involving periods of increased heart activity are needed to detect coronary disease. A preferred embodiment of the present invention will be able to detect coronary occlusion while patients are resting, and without requiring chemical or other inducement of cardiac stress. In this form, the test is much less stressful and can be performed on patients for whom a standard stress test would be difficult to perform or even dangerous.

Both instruments disclosed in the present submission share the same basic detection technology and have similar basic structure.

DETAILED DESCRIPTION OF THE PREFERRED EMBODIMENTS

Figure 1:
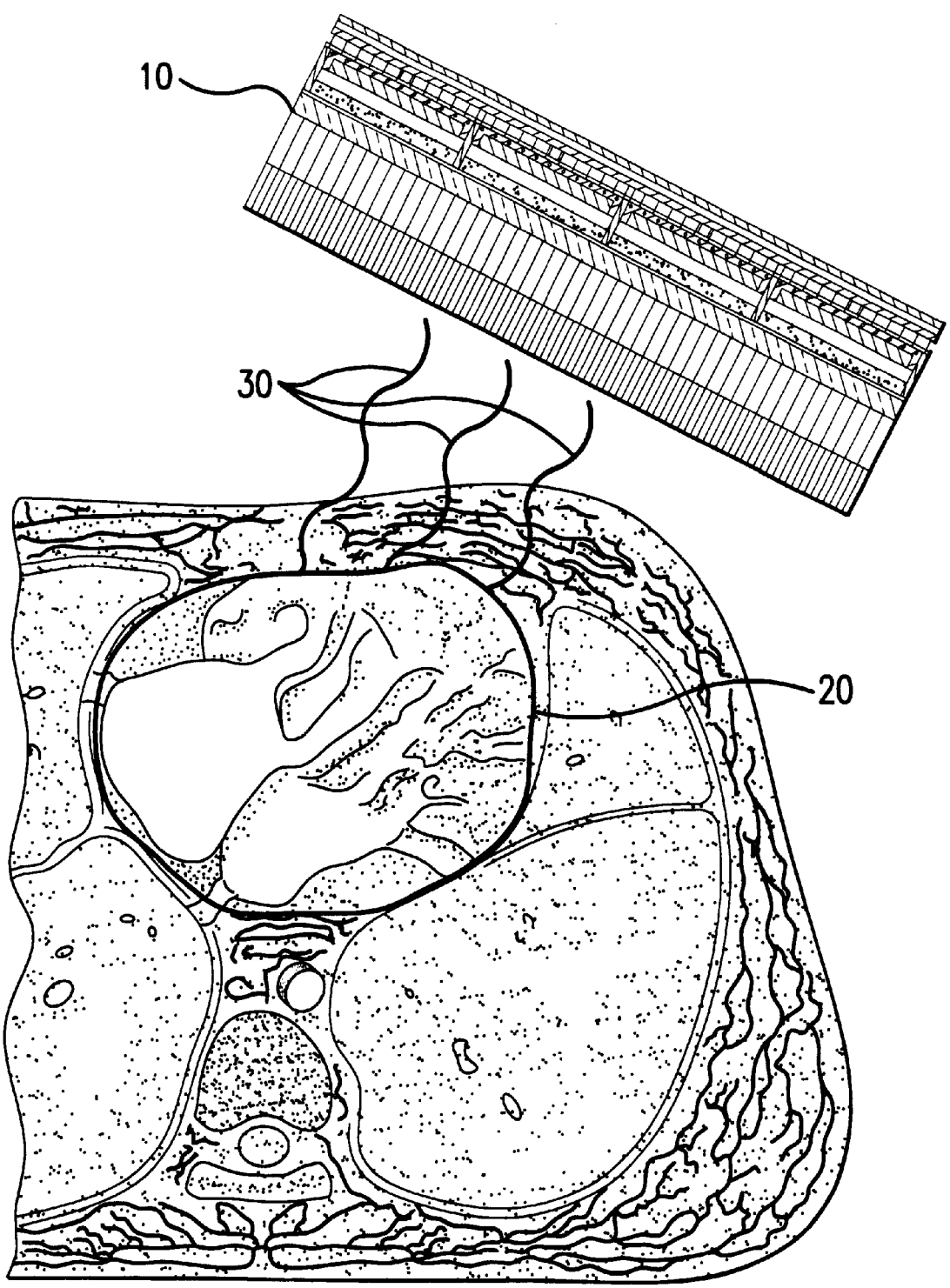
FIG. 1 is a diagram of a single head imaging detector.

FIG. 1 depicts a single detector head cardiac imaging system embodiment of the present invention. The detector head 10 is depicted scanning a heart 20 by detecting emitted gamma rays indicated by wavy lines 30. In a preferred embodiment, the imager will operate in the gamma energy range of 60–600 keV with rate capability approaching 1 MHz. The high rate capability is the result of the system of the present invention including the capability of operating in parallel digital data flow mode for transferring pixellated or digitized information from the digital imaging camera detector 10. This high rate performance will be especially well adapted to the so-called "first-pass" heart imaging procedure. Prior art gamma cameras in medical practice have intrinsic rate capability limited to less than ~100 kHz due in part to their slow front-end electronics and data acquisition systems. The small-size multicrystal camera developed by Picker International, now Marconi, can operate at high rates but has poor spatial resolution, has very limited software capabilities and is very expensive. By a complete redesign of the original Anger camera concept, including combined use of recently developed pixellated crystal scintillators, new fast and compact photomultipliers, dedicated matched light guides, new fast readout electronics and data acquision system, and novel imaging algorithms, the cardiovascular imaging system of the present invention will achieve unprecedented rate capability while offering high sensitivity and high spatial resolution for practically all radiopharmaceuticals used in nuclear medicine, including positron emitters.

Figure 2A:
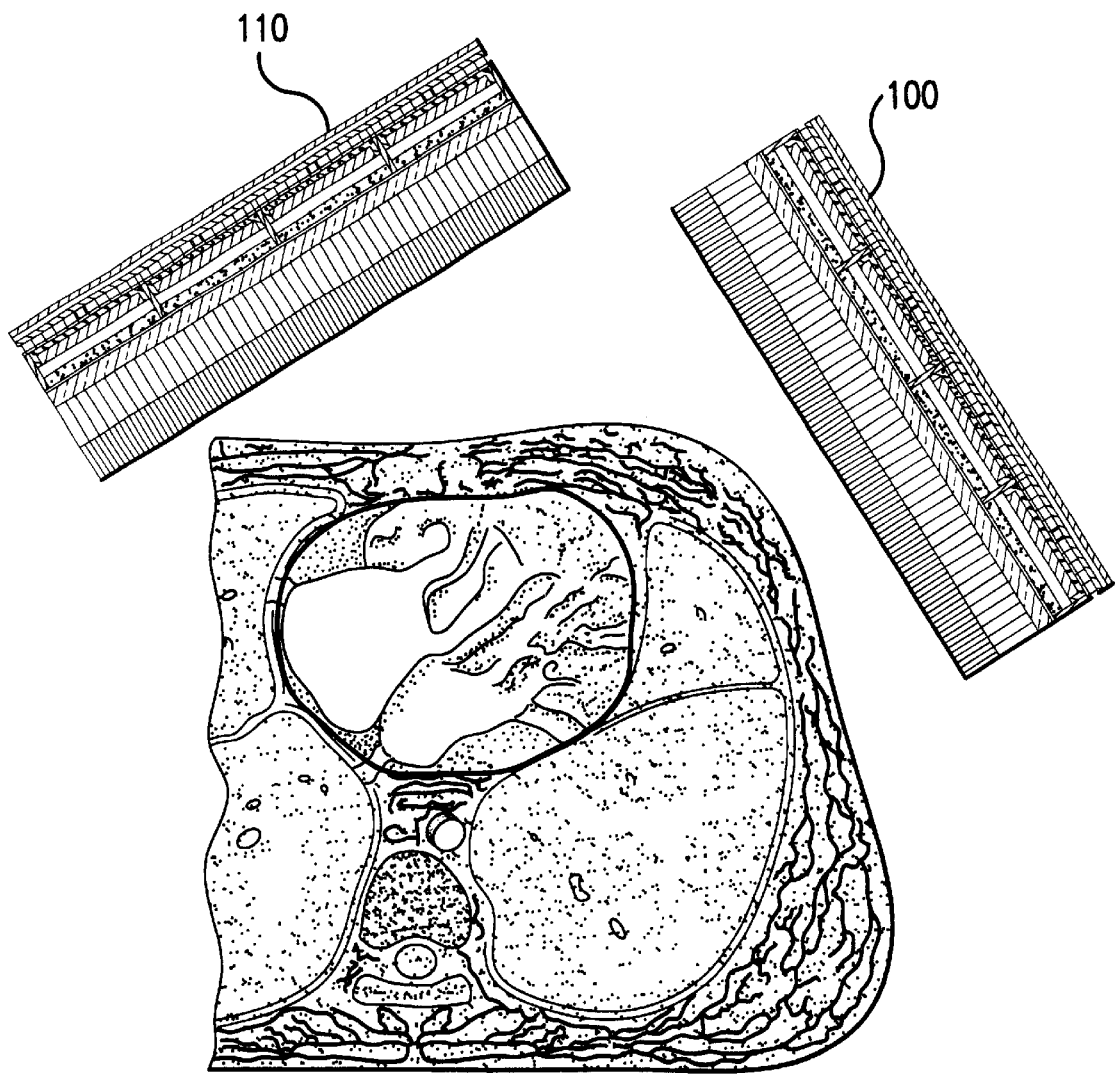
FIG. 2a is a diagram of an embodiment of a two head imaging detector.

As depicted in FIG. 2a, a preferred embodiment of the present invention will include two detector heads 100 and 110. FIG. 2a depicts a cross section viewed from the bottom of the patient, i.e. looking from the direction of the feet. (As will be readily understood by persons of ordinary skill in the relevant technology, inclusion of a second detector head 110 in addition to detector head 100 adds the capability in the present invention of adding a second dynamic view of heart which can be used to simultaneously view all of the edges of the ventricular blood pool. Thus, in addition to the motion of the antero-lateral, apical, and posterior walls (RAO), the septal and posterior-lateral walls are also examined (LAO). Two simultaneous views also increase the accuracy of diastolic chamber volume calculation, A second detector may also monitor the input bolus for deconvolution analysis and quality assurance (bolus shape). Furthermore, wall motion information to correct for heart movement in the first pass test procedure is provided by the second camera 110 being positioned 90 degrees from first camera 100, and therefore imaging at a right angle to the first camera 100 that is looking directly into the patient's heart 20, as depicted in FIG. 2a. In the first-pass test a preferred positioning of the main detector head 100 is approximately 30 degree right anterior oblique. This allows a view perpendicular to the long axis of the cardiac chamber such that valve location can be detected. Valve location is not possible to obtain in equilibrium pool studies. Such a configuration provides the additional utility of permitting the cardiovascular imaging system to calculate stroke volume with this information. All this information will be available after only a 15 second test. In the blood pool (MUGA) studies the preferred position of the head will be 30 degree left anterior oblique. A ~–45 degree tilt angle option can be employed to better align the imaged field of view with the heart chambers.

Figure 2B:
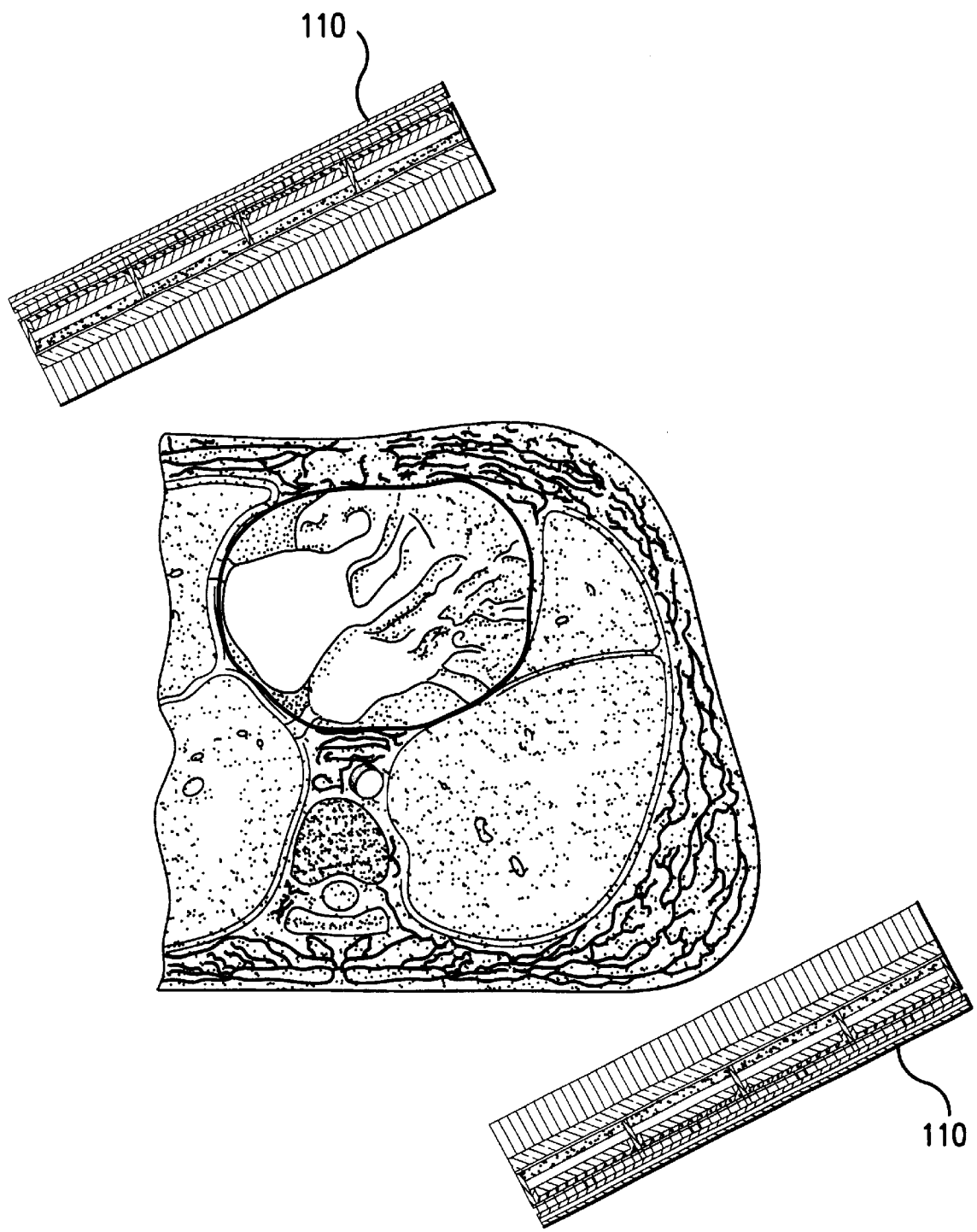
FIG. 2b is a diagram of a second embodiment of a two head imaging detector.

As depicted in FIG. 2b, first camera 100 and second camera 110 in the two detector head system may be configured at 180 degrees relative to each other. In such an embodiment, the system can operate as a positron imager. FIG. 2b also depicts a cross section viewed from the direction of the patient's feet. In principle, a single head system equipped with a special high energy collimator can be used in positron imaging but this result comes at the expense of reduced spatial resolution and sensitivity. Embodiments of the present invention comprising a two head positron imager can operate in a simple planar tomographic reconstruction mode (such as laminography) to produce image slices through the heart.

Figure 2C:
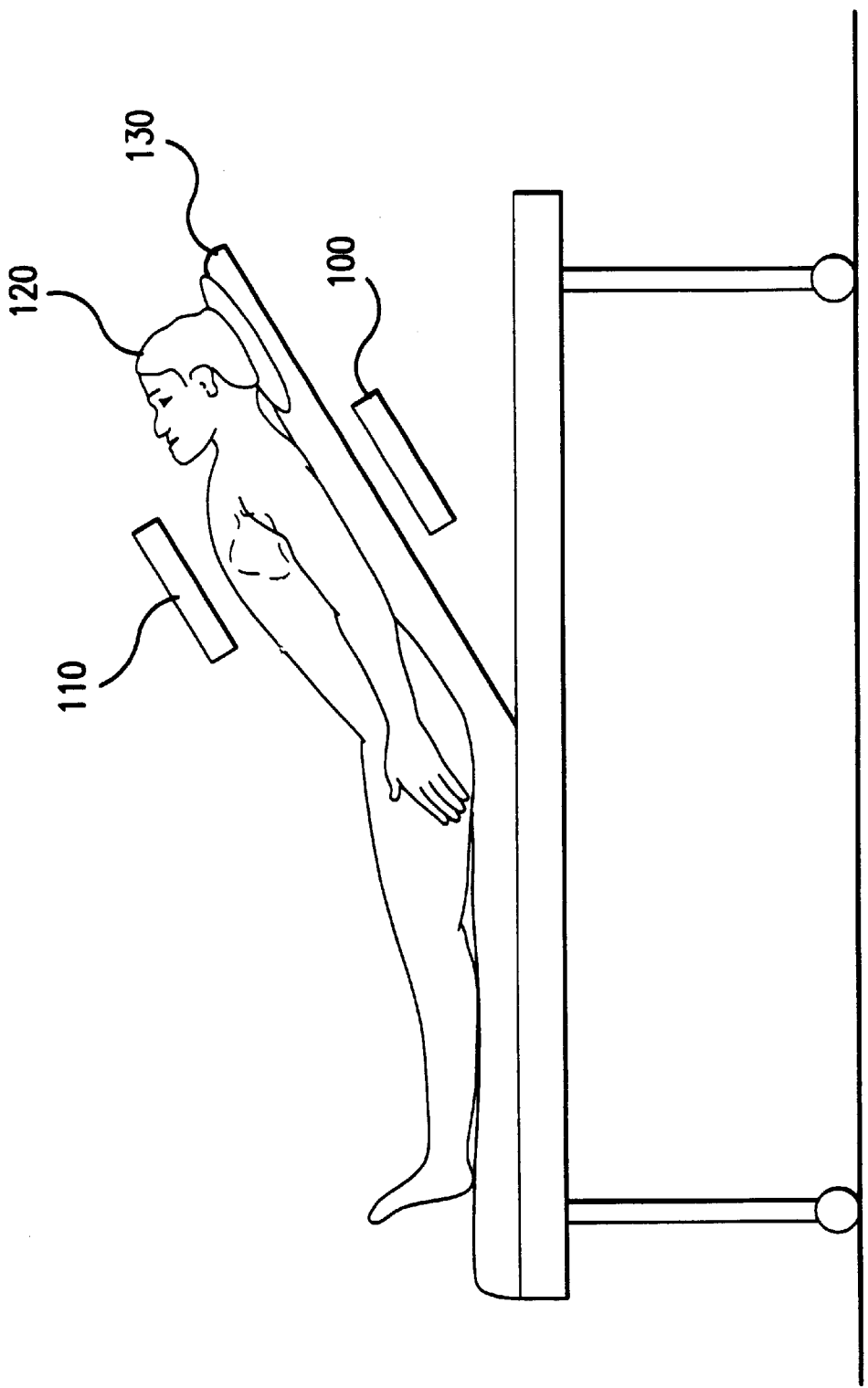
FIG. 2c is a diagram of a third embodiment of a two head imaging detector.

FIG. 2c depicts a third embodiment of the present invention, wherein first camera 100 and second camera 110 in the two detector head system are again configured at 180 degrees relative to each other, this time imaging the heart 20 of a patient 120 reclining in bed 130.

Figure 3:
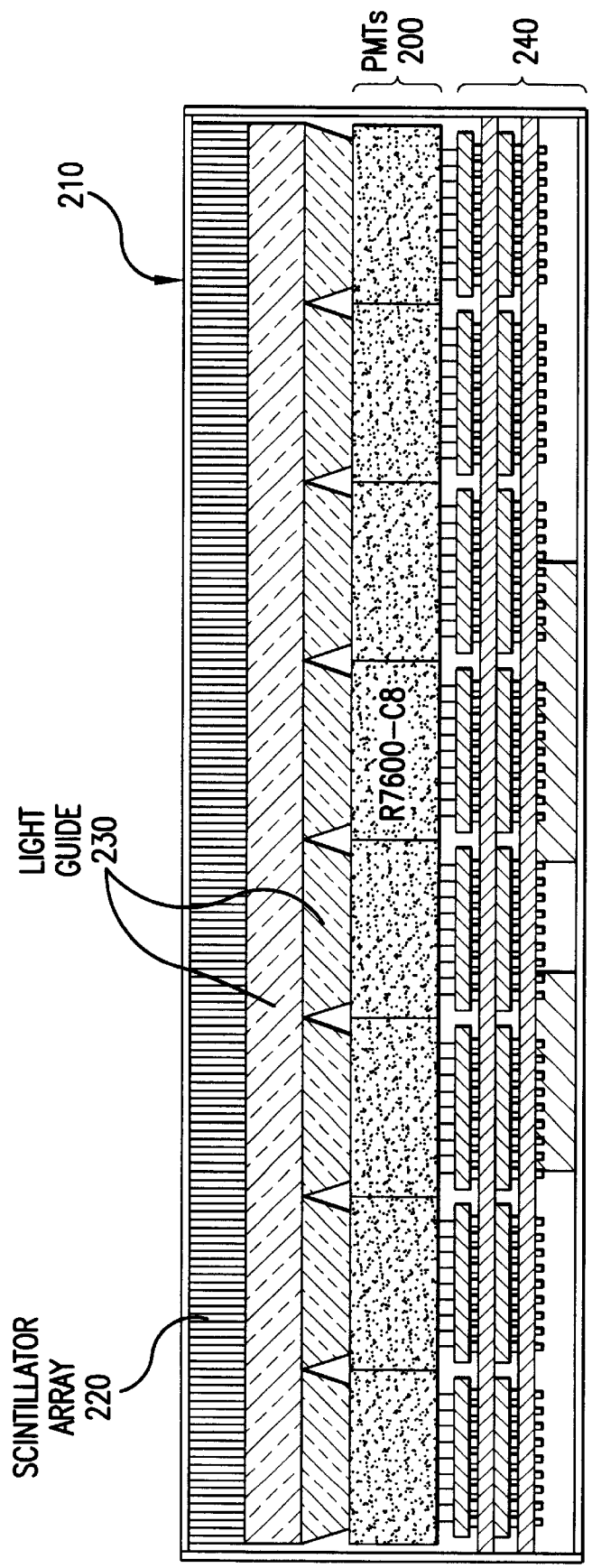
FIG. 3 is a detailed diagram of an imaging detector head.

The cardiovascular imaging system of the present invention applies compact position sensitive photomultiplier technology to develop a novel dedicated fast rate heart gamma imager. The imager provides highly improved spatial resolution and sensitivity to gamma-rays at a lower cost than current clinical nuclear medicine systems. Because of its compact size, this dedicated instrument will also permit new imaging geometries for improved visualization of important prognostic aspects of heart function. To achieve these novel improvements, as depicted in FIG. 3 the imaging technology utilized in the gamma camera element of the present invention is based on an array of compact position sensitive photomultiplier tubes (PMTs) 200 arranged in arrays (such as 6×6, 8×6, 8×8, etc.) to form a single detector head 210. These PMTs are commercially available as Hamamatsu model nos. R7600-C8, R7600-C12 or R7600-M4. The detector head 210 further includes a scintillator array 220 for pixellating or digitizing scintillation light, and a light guide element 230 to direct the pixellated light to the PMT array 200. Fast on-board electronic circuitry 240 processes the signals from the PMT array 200 and directs them to a fast data acquisition system (not shown). The gamma detector head 210 as depicted in FIG. 3 uses a 8×8 array of these PMTs and has an active field of view on the order of 20 centimeters×20 centimeters. A collimator (not shown) may be used with the gamma detector head 210 in single gamma imaging, and is typically placed in front of the scintillator array 220 opposite the light guide element 230.

Figure 4:
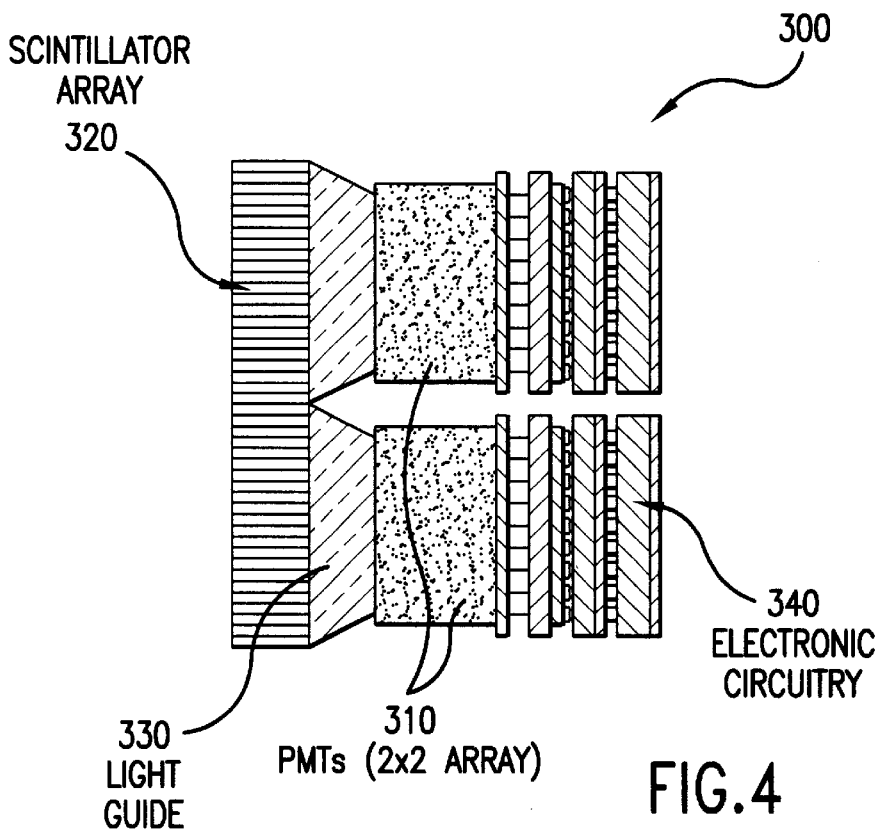
FIG. 4 is a detailed diagram of a preferred embodiment of a sector of an imaging detector head.

In a preferred embodiment the detector head 210 may be built in a modular fashion, shown in finer detail in FIG. 4. Module 300 comprises 4 PMTs arranged in a 2×2 PMT array 310. Scintillator array 320, light guide 330, and electronic circuitry 340 all function as their comparable elements depicted in FIG. 3. The modular design depicted in FIG. 4 allows for high operational rates by subdividing the active field of view of the imager 210 of FIG. 3 into sixteen sectors, each processing information in parallel.

Figure 5:
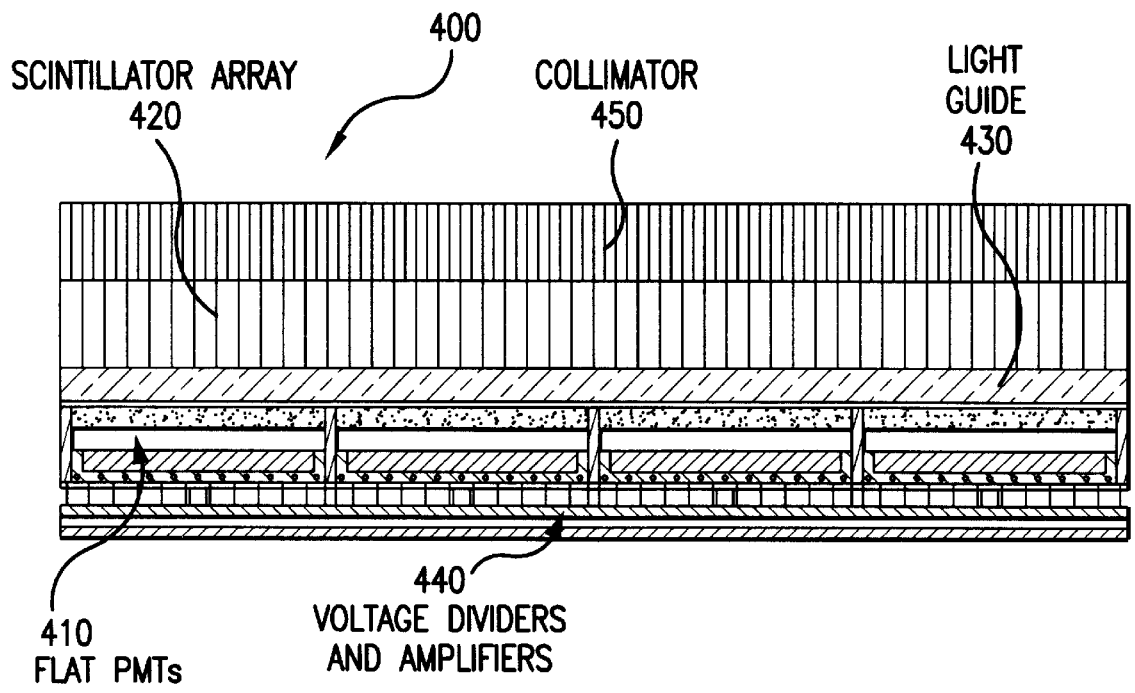
FIG. 5 is a schematic diagram of an improved gamma detection head with flat position sensitive photomultipliers.

FIG. 5 depicts a further improved design of a modular gamma detector head 400. In this design, a flat PMT array 410 is employed to reduce the physical size of the imager 400. The flat PMT array 410 operates in conjunction with scintillator array 420, light guide 430, electronic circuitry 440 and collimator 450 in a manner similar to the above-detailed gamma detector head elements.

Figure 6:
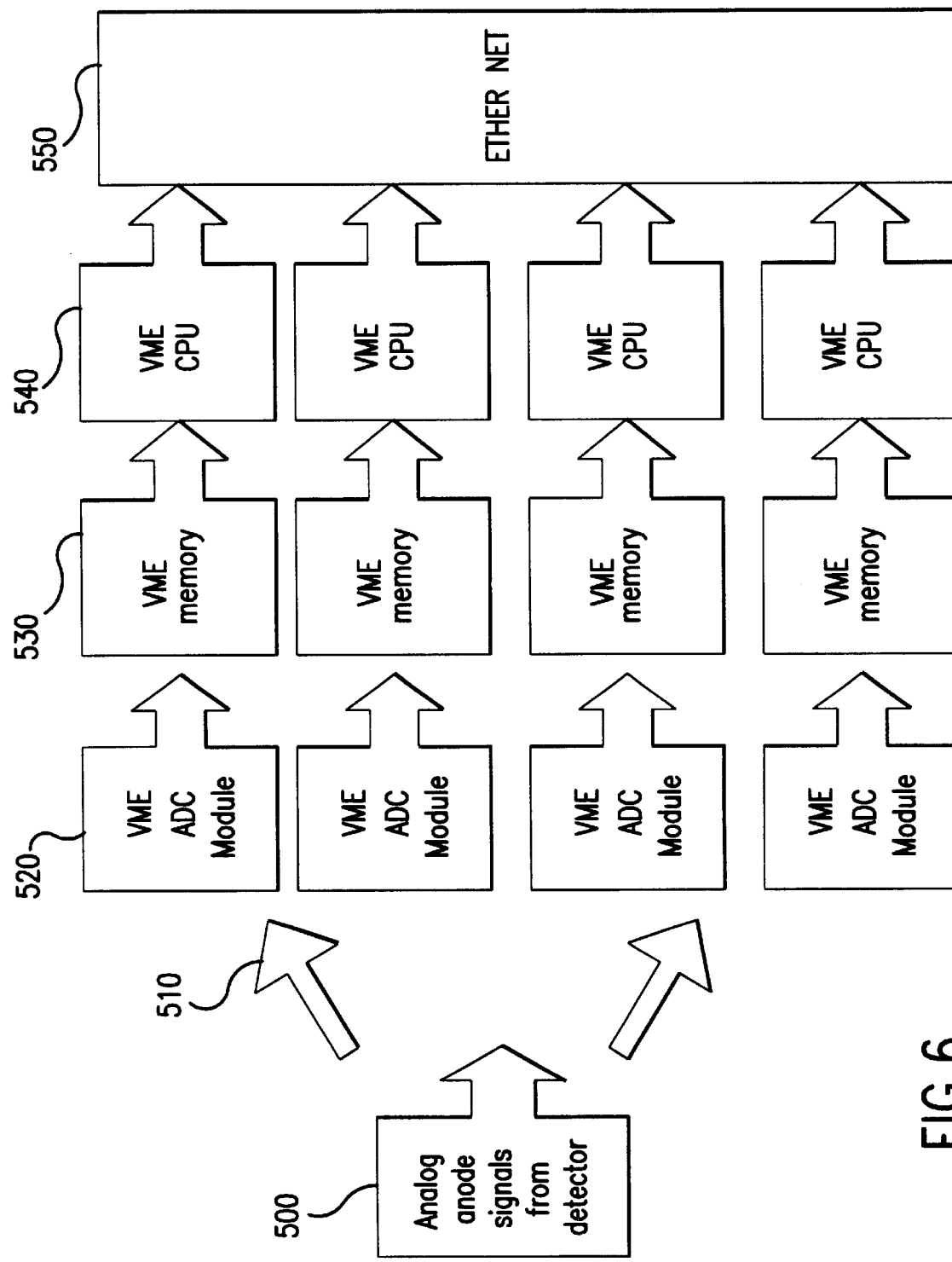
FIG. 6 is a flowchart depicting an example of the data processing system of the present invention.

FIG. 6 displays an example schematic of parallel data flow in the cardiovascular imaging system of the present invention. The analog data signals 500 received from the detector (not shown) are split into parallel electronic channels (paths), shown collectively as 510. As will be appreciated by persons of ordinary skill, any number of channels may be employed, with the intention of insuring rapid data throughput and the elimination of dead time. The data is divided between multiple modules, VME ADC 520, VME CPU 530, and VME memory modules 540. The individual channels communicate via a suitable data network 550 such as Ethernet, using an appropriate data transmission protocol.

Further enhancements not shown, but anticipated in conjunction with the cardiovascular imaging system of the present invention include thick pixellated NaI(T1) scintillator arrays with pixel sizes of 2–5 mm by 20–25 mm thick to detect gamma rays in the broad range from 60–80 keV ((T1-201) to 511 keV (F-18). The scintillator array may be coupled to the photomultiplier array via a special optical window to form very compact detector heads with an active field of view on the order of 20 cm square. It is further contemplated that the detector heads may be attached to a support gantry/harness to provide co-registration with the patient's body. In an imager system with a single detector head at lower energy range, including 140 keV from Tc-99m, a lead collimator may be implemented, while at higher energies, including 511 keV, a tungsten collimator will typically be preferred. In the positron imaging mode two detector heads will be preferably used in coincidence with no collimators attached, as previously described. Enhancing the modular design of the present invention, a set of interchangeable collimators may be employed depending on the required balance between the detector efficiency and its spatial resolution. The detector heads are preferably encased in a ¼–½" thick tungsten shield to avoid unwanted counts from background radiation.

As will be appreciated by persons of ordinary skill in the art, at this time there is no other known imaging modality that can provide the same information and as precisely as the nuclear medicine technique. For example, an ultrasound exam can last up to 30 minutes and will not provide all useful information such as pulmonary transit time, as compared to a 15 second duration of the first pass test providing this information.

As disclosed herein, the cardiovascular imaging system of the present invention in its various embodiments has the capability of performing and/or acquiring the following types of nuclear cardiology studies:

First pass imaging (preferably based on the first heart-beat cycle following the peak of bolus activity to avoid noise from later cycles—closer to equilibrium condition) to evaluate the ejection fraction and transit time of a bolus of radiotracer through heart; planar, gated (and non-gated) blood pool (MUGA) studies to evaluate synchrony of wall motion and elucidate a left ventricle ejection fraction (LVEF); planar, gated (and non-gated) perfusion studies to evaluate blood flow to the myocardium (left ventricle); blood flow in myocardium under stress (not possible with resting LVEF obtained in standard SPECT); coronary artery disease screening; synchronism; planar hot spot imaging; and limited positron detection via planar acquisition to image metabolism within the heart (such as myocardial viability).

Other novel features of the cardiovascular imaging system of the present invention include the following:

Regional cardiac wall motion can be recorded with high contrast, analyzed and promptly displayed;

The high temporal resolution of the system permits regional wall motion and synchrony to be measured;

Infarct sites and abnormalities of conduction can be detected;

When used as a cardiac imager, maximum stress will be of very short duration (10 sec. vs 6 minutes in an equilibrium blood pool test);

The cardiovascular imaging system of the present invention includes flexible and powerful software to analyze and present results in real time, in a user-defined and friendly format;

The device can image Tc-99m (140 keV) as well as other imaging agents that are entering into the imaging arena such as In-111 (173 keV, 247 keV), and I-123 (159 keV). The preferred radiotracer tagging the blood to be used in the above procedures is In-113 m (390 keV) with 90 minute half-life. The advantage of higher energy vs. 140 keV of Tc-99m-Sestamibi is that absorption correction will be much less important. For example in women attenuation of 140 keV photons in radiodense breasts produce attenuation artifacts in heart imaging, potentially obscuring blood flow deficiencies.

Furthermore, the system will have a unique ability to image 511 keV photons from positron emitting radiotracers such as F-18-FDG. The widespread use of unit dose pharmacies with F-18-FDG, as well as newer positron emitters (Cu-62-PTSM) for cardiac imaging make this positron imaging option financially viable.

Other competing or potentially competing technologies for dedicated heart imagers, such as CdZnTe solid state detectors (developed by Siemens, GE Medical), CsI(T1) scintillator/silicon photodiodes (Digirad), and gas based detectors (Proportional Technologies) are not capable of efficiently imaging positron emitters.

The preferred solution of using one universal scintillator pixel array is the most efficient method to obtain the two-in-one dual modality gamma imaging system. Three known preferred pixellated scintillator choices are the following: 1" thick NaI(T1), ~2–3 cm thick Gadolinium Oxyorthosilicate (GSO), and ~2 cm thick Luthetium Oxyorthosilicate (LSO). GSO and LSO scintillators are faster and have higher stopping power for 511 keV photons than NaI(T1) but are much more expensive and have lower energy resolution (resulting in lower scatter rejection) for lower energy photons, such as 140 keV from Tc-99m.

As disclosed herein, a preferred embodiment of the cardiovascular imaging system of the present invention will include the following features, each of which, in conjunction with the above detailed description, will be familiar to those of ordinary skill in the relevant technology:

One or more "heart size", compact and easy maneuverable ~20 cm×20 cm gamma camera heads with broad energy range, high rate and high spatial resolution response;

Fast signal processing electronics and fast data acquisition system;

Gantry for control electronics and computer;

Support arm(s) for the detector head(s) with optional patient vest;

Computer system with data processing algorithms;

Digital data storage system; and

High quality monitor and hardcopy printer.

EXAMPLE OF A PREFERRED EMBODIMENT

To enhance further the understanding of the cardiovascular imaging and functional analysis system disclosed herein, the following example of a specific embodiment of the present invention is presented. As disclosed, the example presented is a Cardiovascular Non-Invasive Screening Probe System and Method for Coronary Artery Disease.

The components of the exemplary Non-Invasive Screening Probe System include the following:

Two dedicated gamma probes

Fast signal processing electronics and fast data acquisition system

Gantry for control electronics and computer

Support arm(s) for the detector probes

Computer system with data processing algorithm

Digital data storage system

Hardcopy printer

Figure 7A:
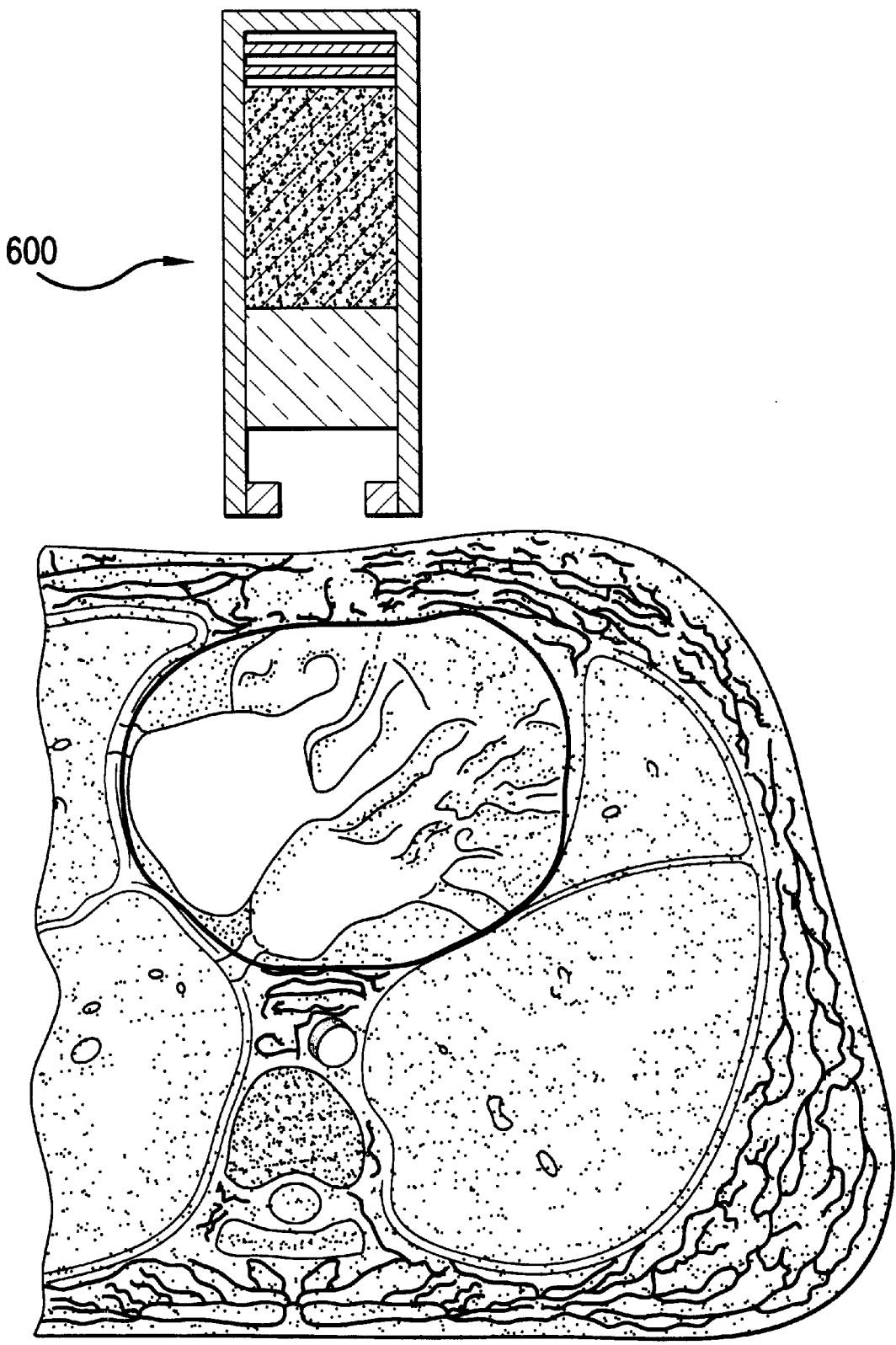
FIG. 7a is a diagram of a gamma detection probe in use.

The exemplary Non-Invasive Screening Probe System, as proposed, will provide an economical instrument to ascertain coronary artery disease. During the screening procedure, the patient is injected intravenously with a bolus of radioactive tracer (e.g., with several ml of 1–20 mCi of Tc-99m DTPA (15–20 min half live) in the antecubital vein in the right or left arm or 100–300 mCi of hippuran labeled with I-131). The passage of the injected bolus is monitored by two dedicated gamma probes. The first reference probe is positioned over the chest wall over the aorta FIG. 7a shows the position of second gamma probe 600 from the top, or from the direction of the patient's head. Second gamma probe 600 is shown recessed in collimator 610.

Figure 7B:
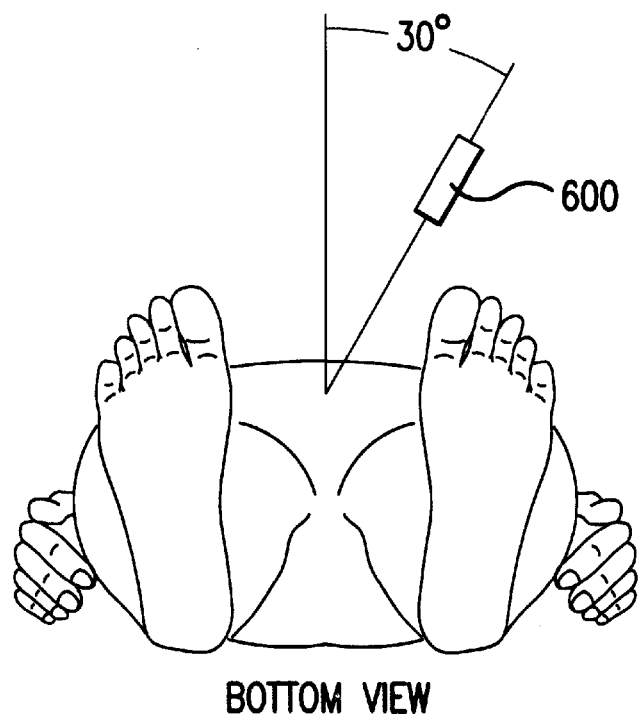
FIG. 7b is a diagram of the positioning of a gamma detection probe.
Figure 7C:
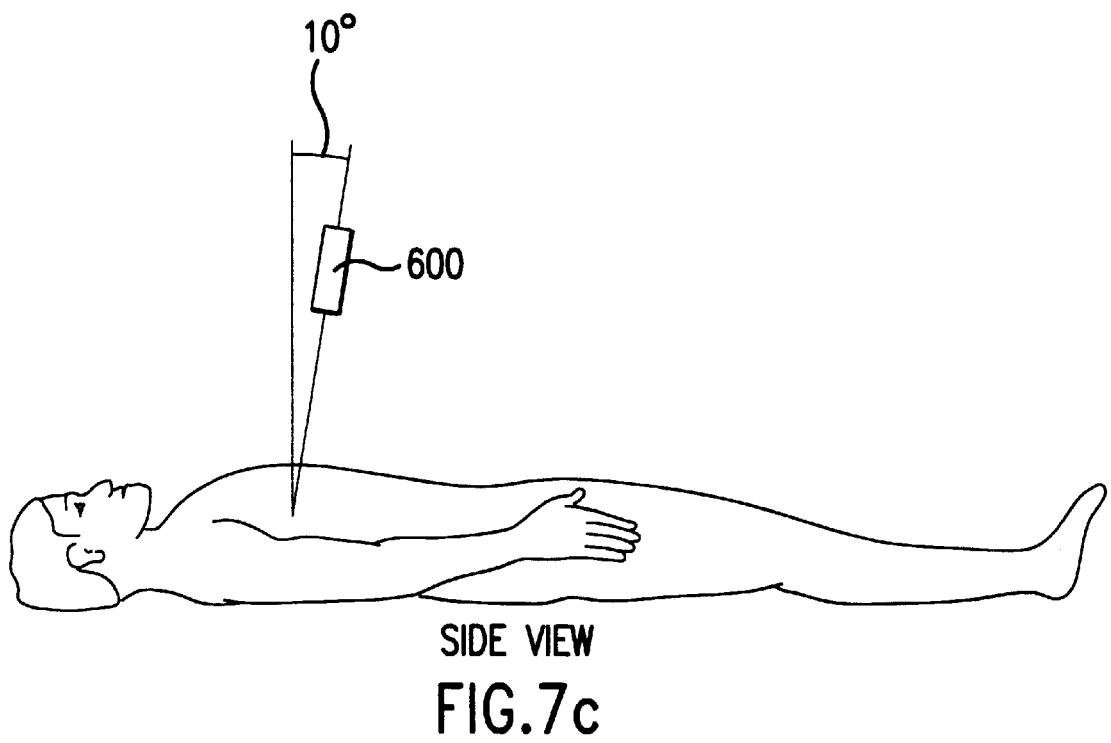
FIG. 7c is a second view of the positioning of the gamma detection probe shown in FIG. 7b.

FIG. 7b shows in further detail the preferred placement of the second gamma probe 600 in both a bottom view and a side view. The second gamma probe 600 is positioned over the left ventricle, beginning in a vertical left-to-right (axial) plane perpendicular to a horizontal side-to-side (coronal) plane angled to align with the axis of the left ventricle, approximately 30 degrees toward the patient's left side and 10 degrees toward the feet in a vertical head-to-toe (parasagittal) plane.

To ensure that the injected bolus is not fractionated (broken), a separate monitor probe may be added to monitor the quality of the injection, in order to allow for proper analysis.

Coronary Transit-Time Screening

Figure 7D:
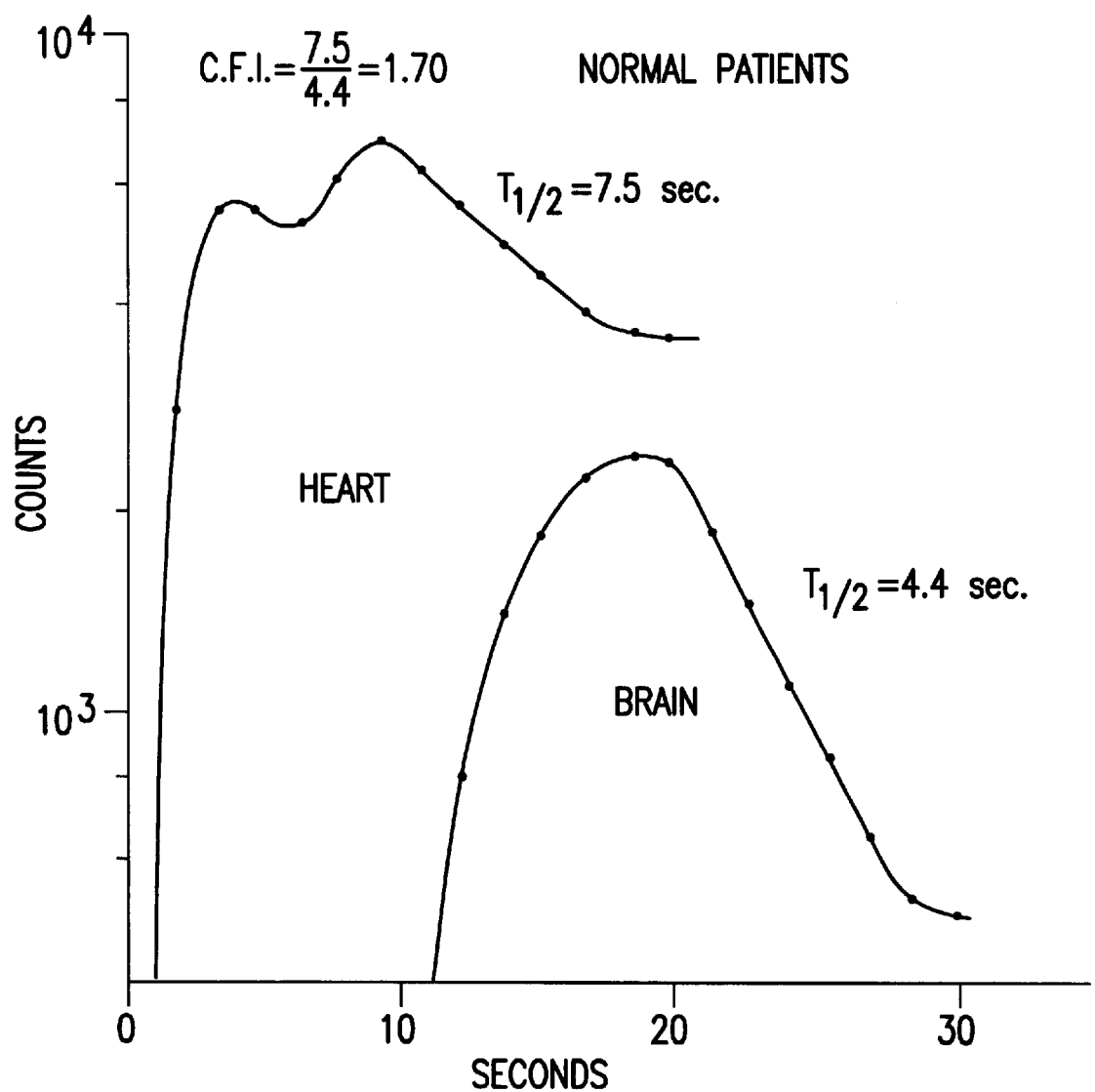
FIG. 7d is a graphical representation of low frequency time activity curves of the same bolus measured for the left heart region and a downstream region for a normal patient, as determined in accordance with an embodiment of the present invention.
Figure 7E:
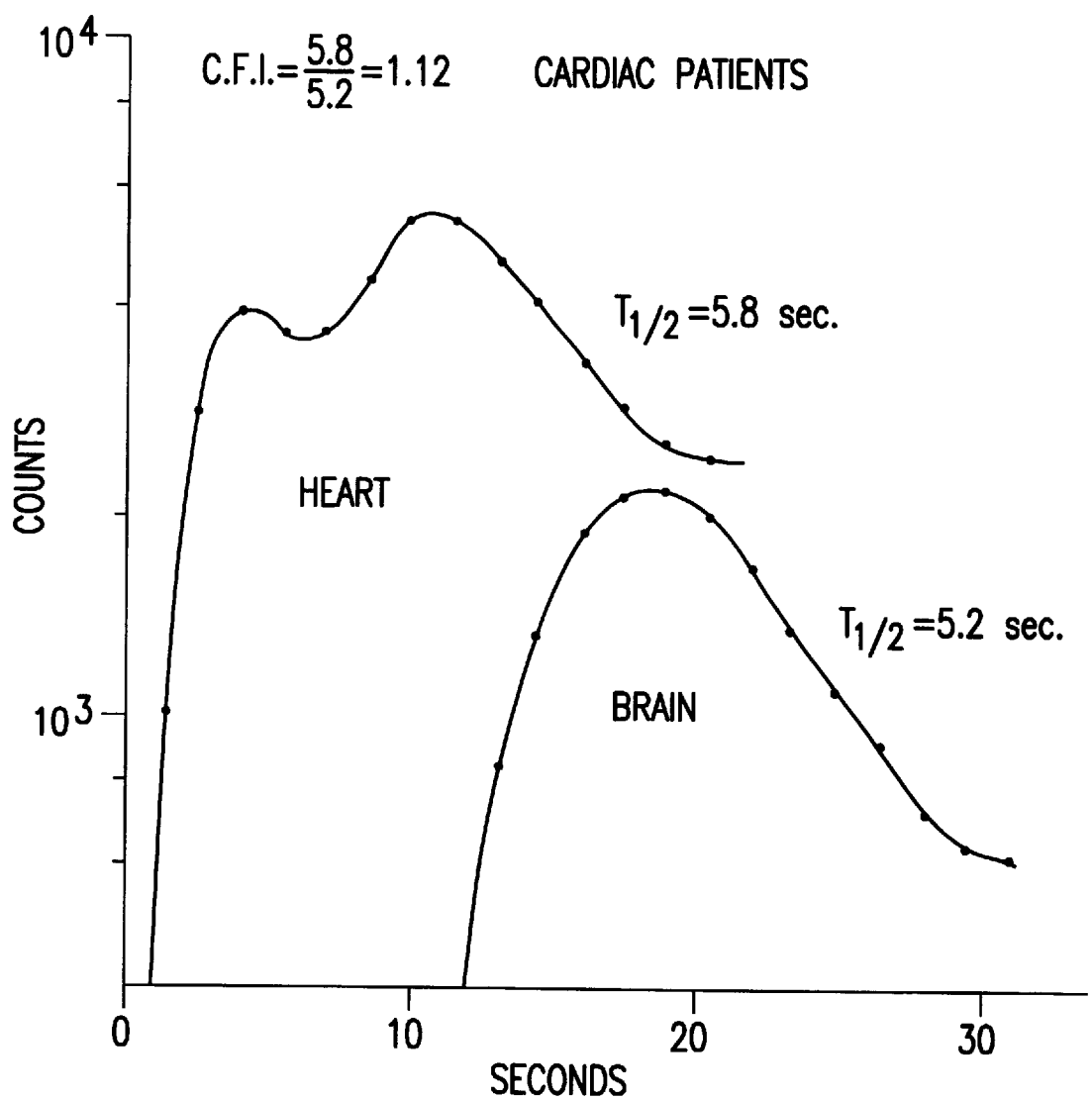
FIG. 7e is a graphical representation of low frequency time activity curves of the same bolus measured for the left heart region and a downstream region for a cardiac patient, as determined in accordance with an embodiment of the present invention.

In accordance with the principles of the present invention, following the rapid injection of a small volume of gamma emitting isotope into a peripheral vein, a collimated radiation detector positioned over any portion of the body surface will respond to the primary (i.e., just after injection) passage of this radioactive bolus as it travels through the vascular channels in its field of detection. This response is referred to as the "time-activity curve". The small volume of the isotope originally injected is diluted and elongated as it traverses the circulation. Consequently, the time-activity curves become gradually more prolonged as they are recorded by similar detectors (probes) at increasing distances from the point of injection. This prolongation can be associated with decreased rates of disappearance of radioactivity at any point of observation. In other words, the slope of the descending portion of the time-activity curve decreases as the bolus is elongated. This "washout" of an externally measured radioactive tracer bolus from the region of the heart is normally slower than the washout of the same bolus from the ascending aorta. The prolongation of the slope of the descending portion (downslope or washout slope) of the left heart time-activity curve, relative to slopes produced by the same radioactive bolus downstream in the circulation, has been demonstrated in animals and in human subjects, consistent with the current example of the present invention. Data collected from the probe configuration shown in FIG. 7a was used to create FIGS. 7d and 7e, which depict the low frequency time activity curves of the same bolus measured for the left heart region and a downstream region (the back of the head in this case). This information has been published as "Evaluation of an Isotope Coronary Patency Test by Angiography," Radiology, Vol. 81, No. 3, Pages 428–436, September, 1963. Differences between the normal patient of FIG. 7d and the coronary patient of FIG. 7e can be seen.

The double-peaked structure of the heart time-activity curve is due to bolus passage sequentially through the right and left ventricles. A relative difference in downslopes can be observed in the normal patient versus similar downslopes in a patient with occlusive coronary disease. The curve difference may be quanitated by the ratio of slopes. In the figures, this is the ratio of the monoexonential half-times of the left heart and downstream curve downslopes. The coronary transit time index (CTTI) is a ratio of the downslope from the heart over the downslope from a downstream region (in brain in this example). The CTTI ratio for coronary patients is much closer to unity than for normal patients.

Total coronary flow is maintained by dilatation of the distal coronary circulation. Normal coronary arteries accumulate the tracer more rapidly (even though the flow velocity is lower). Thus, as shown below, the shape of the coronary portion is different between normal (FIG. 7f) and coronary (FIG. 7g) even though total flow may be the same. The difference is the shape of the coronary activity time curve. The aortic curve estimates the "true" left ventricle (LV) curve.

Figure 7F:
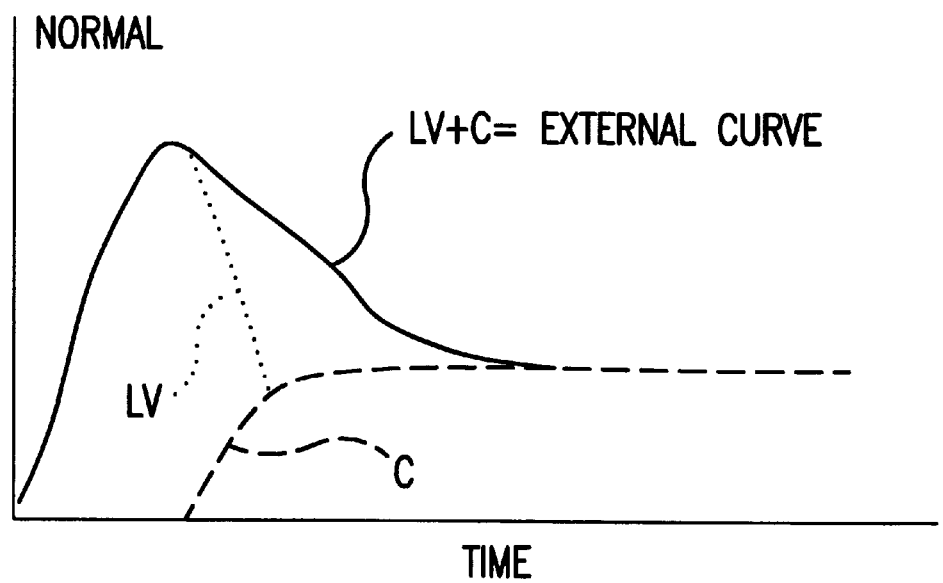
FIG. 7f is a graphical representation of the results of mathmatical and hydrodynamic modeling of the externally detected activity from the first transit of a radioactive tracer bolus through the left ventricle and coronary circulation for a normal patient, as determined in accordance with an embodiment of the present invention.
Figure 7G:
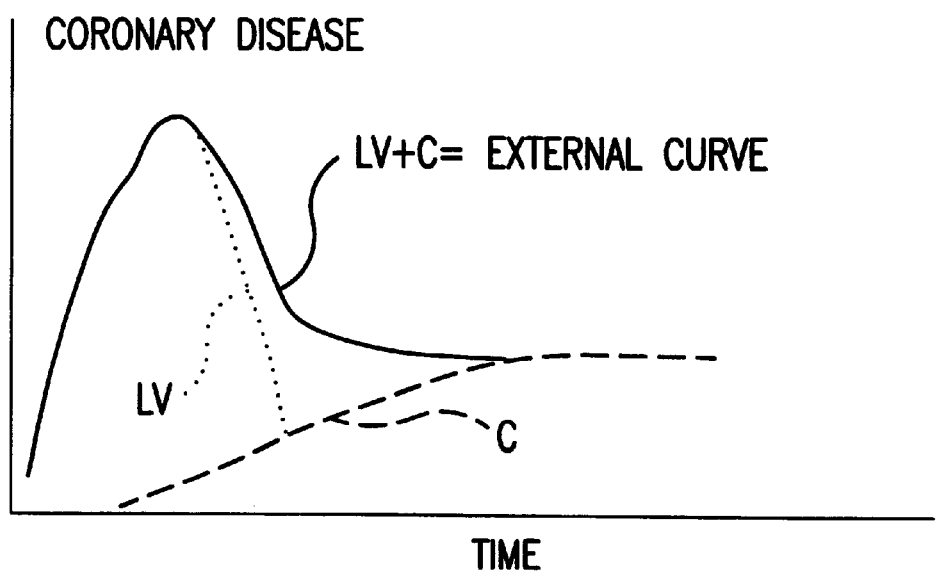
FIG. 7g is a graphical representation of the results of mathematical and hydrodynamic modeling of the externally detected activity from the first transit of a radioactive tracer bolus through the left ventricle and coronary circulation for a coronary patient, as determined in accordance with an embodiment of the present invention.

FIGS. 7f and 7g represent the results of mathematical and hydrodynamic modeling of the externally detected activity from the first transit of a radioactive tracer bolus through the left ventricle and coronary circulation. "A" is the predicted washout of tracer from the left ventricle without the contribution from activity entering the coronary circulation, It may be estimated from the curve of the ascending aorta. "LV+C" is the externally detected curve representing the LV and the onset of coronary filling during LV washout. These models incorporate the established fact that the mean transit time of tracer particles through the coronary circulation is 6–9 times greater than through the LV chamber. Using coronary flows in the range of 4% of cardiac output the models predict not only the prolongation of the external left heart downslope but also the magnitude of this effect. Also predicted is a reduction in the prolongation due to a reduction in 5 volume and/or flow in the coronary circulation. Further as shown in FIGS. 7f and 7g above, the difference in washout times of these two curves is diminished and shifts towards unity in subjects with coronary occlusive disease. The difference between coronary and normal patients is in the long transit-time component of the left-heart activity-time curve. This component is reduced in patients stricken with coronary occlusive disease. This test conducted in accordance with the principles of the system of the present invention has been shown to detect the presence of significant coronary occlusive disease in resting patients with normal ventricular function. As noted earlier, these results-historically available only through stress testing-are obtainable using the system and methods of the present invention, from patients at rest, without requiring physical-induced or chemical-induced stress.

Further in accordance with the principles of the cardiovascular imaging system of the present invention, the exemplary Non-Invasive Screening Probe System will have two highly efficient gamma detection probes: one placed on the chest wall above the aorta, and the second gamma detection probe 600 in the left ventricular region as depicted in FIG. 7a. Use of a multi-element detector described herein can be used to replace the simple probe 600 and avoid the effects of probe mispositioning by the operator. By design, the gamma detection probes will have much higher sensitivity than standard gamma detection devices used today in nuclear medicine. The system will be also much less expensive than traditional gamma camera systems, as it will be only dedicated to the particular screening procedure.

In the exemplary Non-Invasive Screening Probe System the first probe is made out of a single crystal scintillator (or a pixellated scintillation array made from crystal scintillator material) such as NaI(T1), LSO, GSO, CsI(T1), YSO, CsI(Na) etc. The size of the first probe will be approximately 1–2" square and thick enough to detect efficiently gamma photons up to 511 keV. In a preferred embodiment of the exemplary Non-Invasive Screening Probe System, a single or pixellated NaI(T) crystal of ~3×~3×3 cm in size is used in the first probe. A collimator is located in front of the probe and is made of lead or tungsten. The first probe has a single large hole (single bore) or is made of a multitude of smaller holes (e.g., 5-mm in diameter) placed in front of the probe, between the chest wall and the gamma detector/probe.

Figure 8:
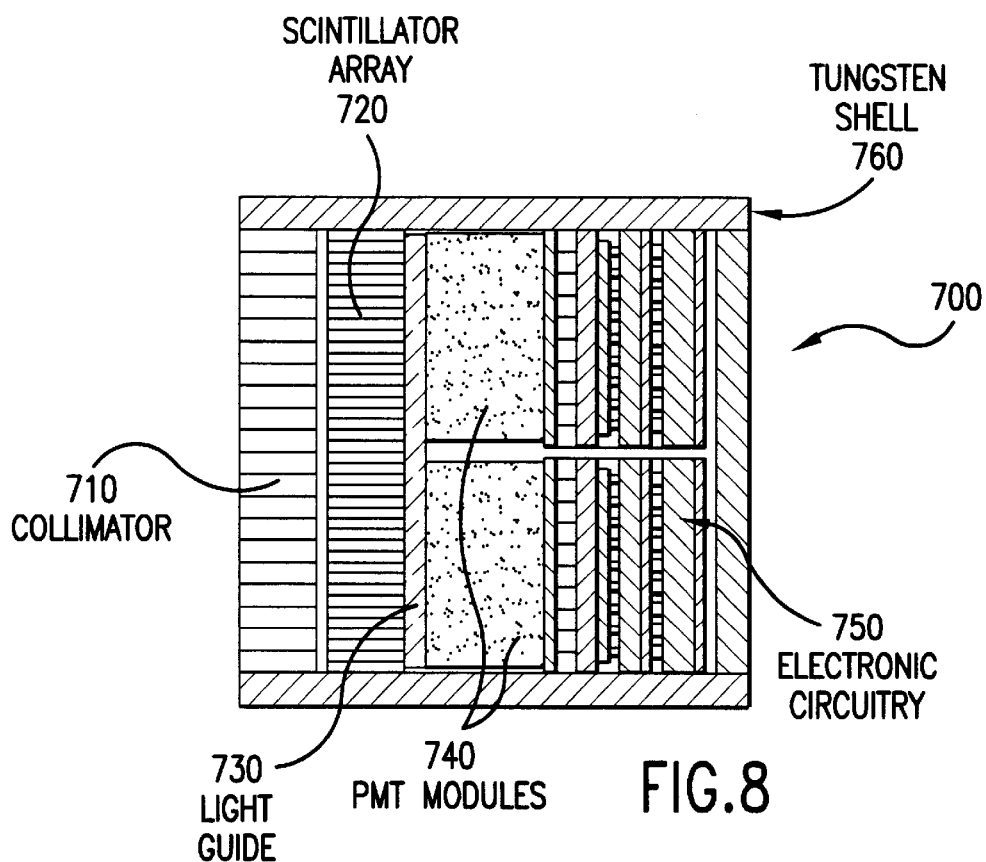
FIG. 8 is a schematic diagram of a specific embodiment of an improved gamma detection probe.

FIG. 8 depicts the second gamma imaging probe 700 of the exemplary Non-Invasive Screening Probe System. The second probe 700 has an approximately 5×5-cm active field of view and is built out of a multitude of smaller-size crystals/pixels. The range of transversal pixel size could be from 3 mm to 20 mm, but typically they will be in the 5 to 10-mm range. A collimator 710 aligns the received gamma radiation before directing it to the scintillator array 720. The second probe 700 of the exemplary Non-Invasive Screening Probe System is made out of an array of crystal scintillator pixels such as NaI(T1), LSO, GSO, CsI(T1), YSO, CsI(Na), etc. Further as in the case of the first probe, in the second gamma imaging probe 700 the thickness of the material will be chosen to accommodate the energy range from 60–511 keV. In the specific embodiment depicted in FIG. 8, the scintillator array 720 uses a thick NaI(T1) pixellated scintillator. In this embodiment of the exemplary Non-Invasive Screening Probe System, the scintillator crystal array 720 typically will consist of ~5×5×25-mm3 pixels that are optically separated by thin (0.2–0.3 mm) white diffusive layers. Four ~1"-square Hamamatsu R7600-M4, R7600-C8,or R7600-C12 PSPMTs arranged in a compact 2×2 array can be used to detect and define the position of a scintillation flash from the gamma conversion in the scintillator array 720. Further as depicted in FIG. 8, light guide 730, photomultiplier tube modules 740, and electronic circuitry 750 perform functions as earlier described in accordance with the principles of the present invention. In the exemplary preferred embodiment depicted in FIG. 8, the gamma detector probe is contained in a tungsten housing 760.

Figure 9:
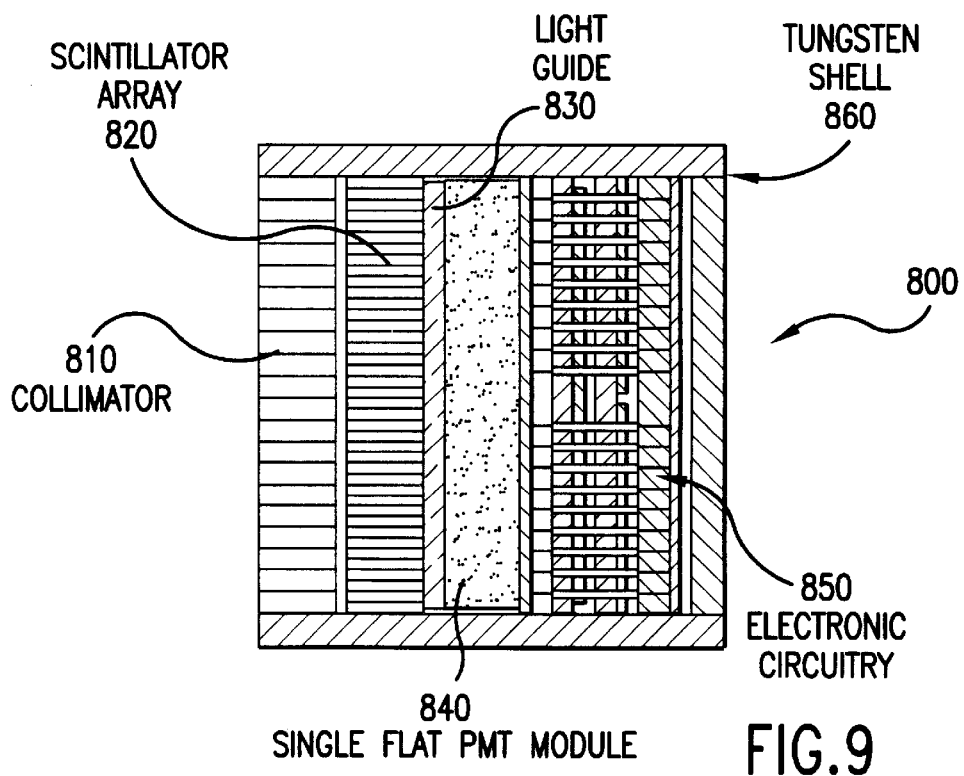
FIG. 9 is a schematic diagram of a specific embodiment of an improved gamma detection probe.

FIG. 9 depicts an improved embodiment of the second gamma imaging probe 800 of the exemplary Non-Invasive Screening Probe System. As shown in FIG. 9, collimator 810, scintillator array 820 and light guide 830 perform functions similar to those in the embodiment in FIG. 8. The photomultiplier tube array 840 in the improved embodiment shown comprises one or more flat PMT modules, which function to reduce the overall size of the probe 800 while permitting closer fit between probe components, which results in substantially improved scintillation light collection, as well as further maximizing efficiency of gamma radiation detection. As shown in FIG. 9, the PMT array 840 comprises a single flat PMT module for maximum space efficiency. Electronic circuitry 850 collects the data received from the PMT array 840, and the gamma imaging probe is preferably contained in a tungsten housing 860.

Figure 10A:
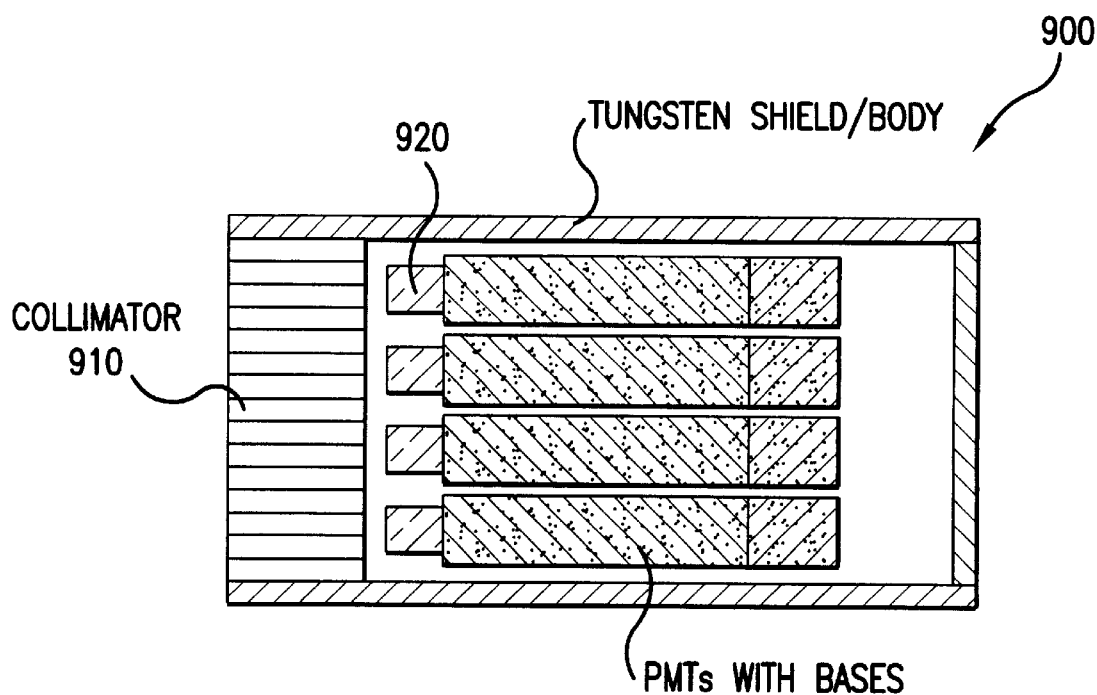
FIG. 10a is a side view cross sectional diagram of a specific embodiment of an improved gamma detection probe.
Figure 10B:
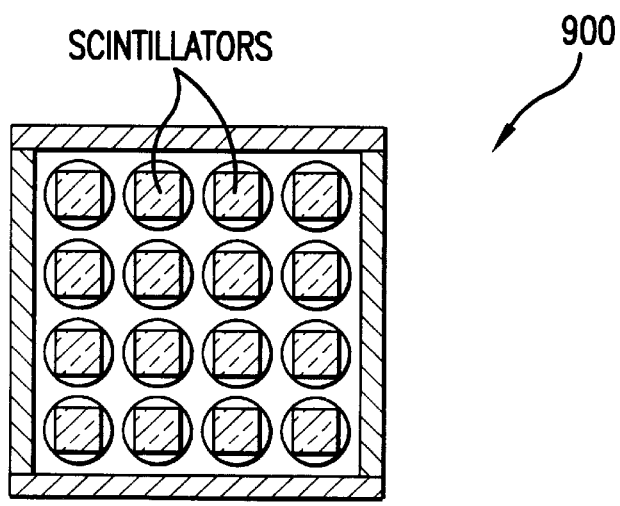
FIG. 10b is an end view cross sectional diagram of a specific embodiment of an improved gamma detection probe.

FIG. 10*a* depicts a side view cross section of an additional improved embodiment of the second gamma imaging probe 900 of the exemplary Non-Invasive Screening Probe System. As shown in FIG. 10*a*, collimator 910 directs incoming light to a scintillator array 920 that is arranged as a 4×4 matrix of GSO scintillators, wherein each individual scintillator in the array is coupled to an individual photomultiplier tube in the PMT module 930. The coupling of scintillator with individual PMT eliminates the need for a light guide, thus further simplifying and improving the exemplary Non-Invasive Screening Probe System, in accordance with the principles and objects of the present invention. FIG. 10*b* depicts the specific arrangement of the 4×4 matrix of GSO scintillators in the gamma imaging probe 900.

Figure 10C:
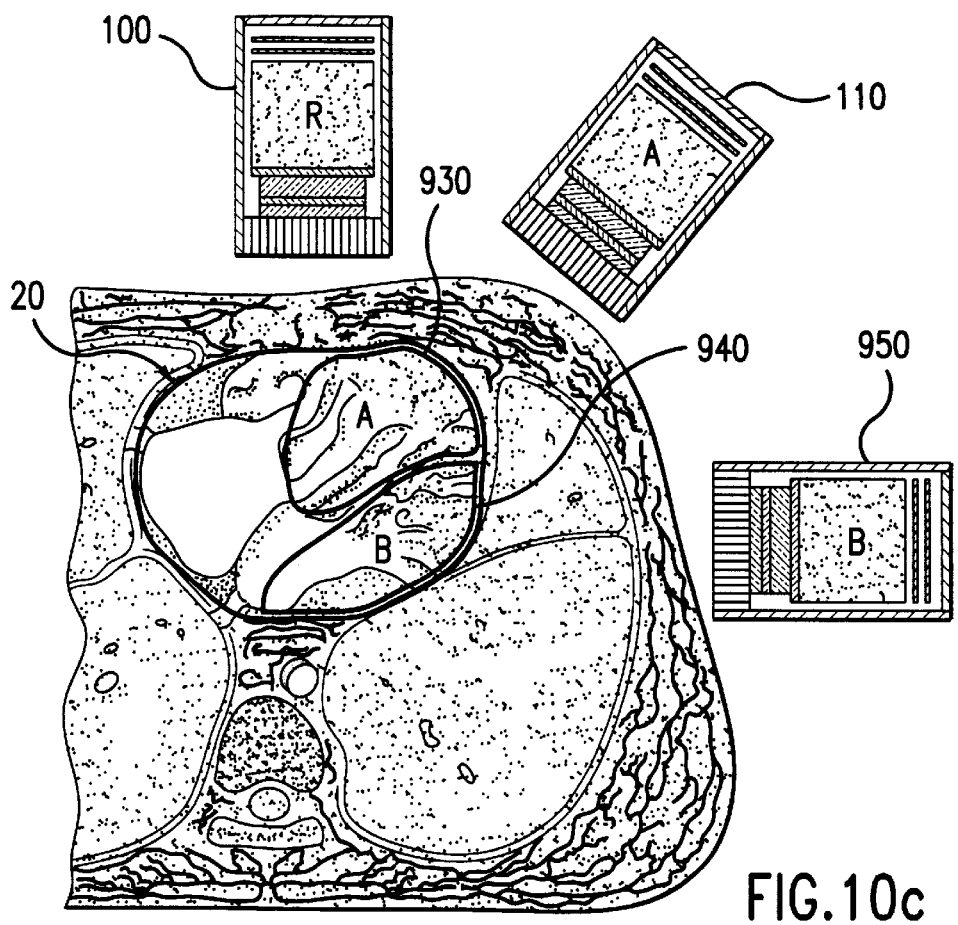
FIG. 10c is a cross sectional diagram of a three probe system embodiment of the present invention.
Figure 10D:
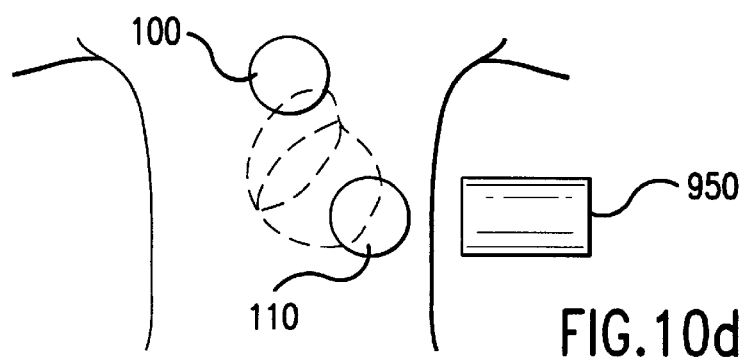
FIG. 10d is a front external of a three probe system embodiment of the present invention.
Figure 10E:
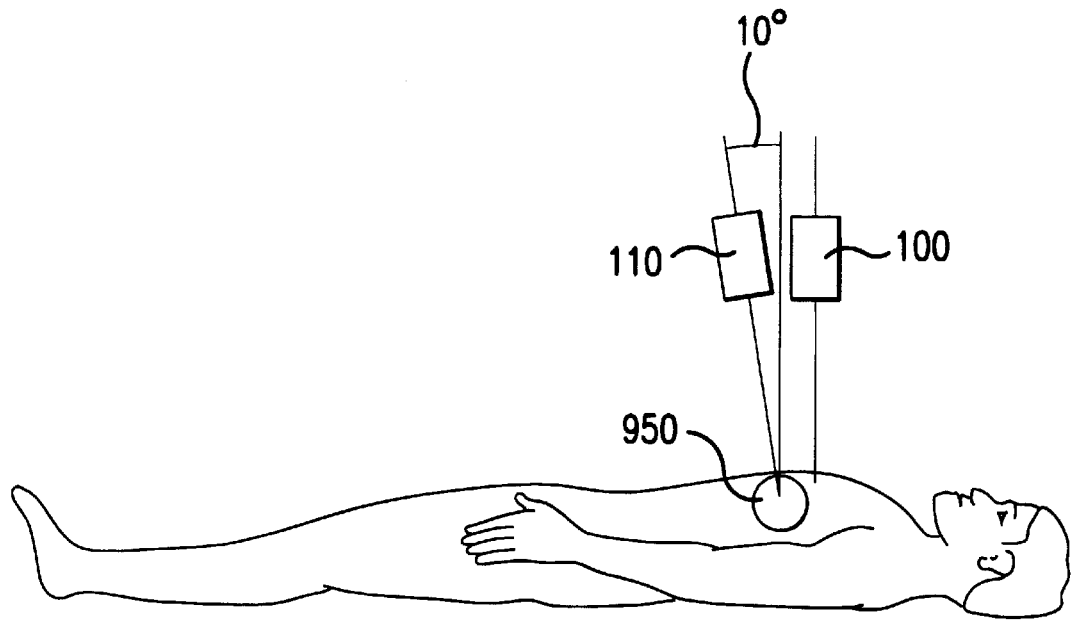
FIG. 10e is a side view cross sectional diagram of a three probe system embodiment of the present invention.
Figure 10F:
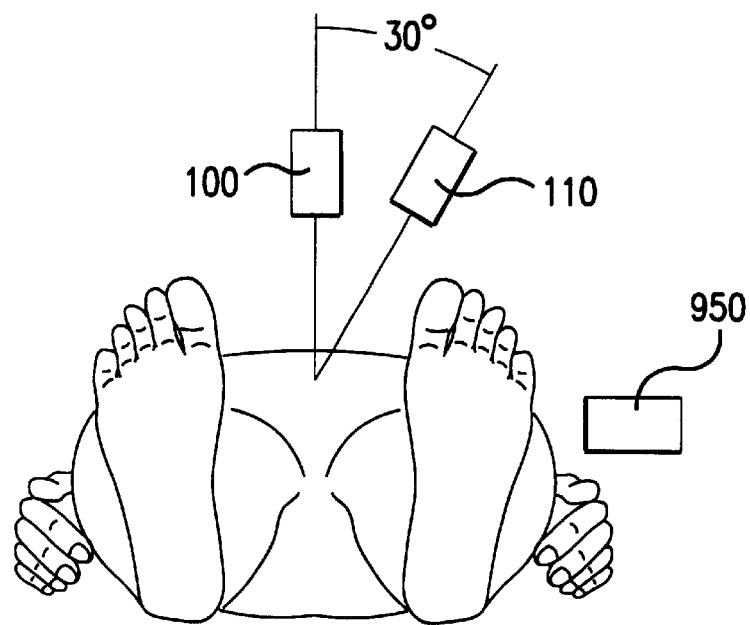
FIG. 10f is a bottom view cross sectional diagram of a three probe system embodiment of the present invention.

When performing the screening test with radiopharmaceuticals labeled with Tc-99m (140 keV gamma emission) or other isotopes emitting lower energy gamma radiation, absorption and scattering of gamma radiation on its way to the gamma detector-probe decreases sensitivity for gamma emissions on the further side of the heart away from the second probe. In FIG. 10*c*, the two cardiovascular regions of heart 930 and 940 each have quite different relative positions vs. the position of the standard second probe 110 as used in the standard two-probe arrangement described before. Probe 100 is used as the first, reference probe positioned above the aorta, as described before. This effect may limit relative sensitivity of the screening test to the cardiovascular problems in the more distant part of the heart. Therefore, to compensate for this near-far asymmetry in the sensitivity of the screening test, a third probe 950 may be added. This probe is identical in construction to the second probe 110 and is positioned in such a way as to view part 940 of heart 20 from much closer distance than the second probe 110. The relative external position of each of the three probes is shown in FIGS. 10*d*, 10*e*, and 10*f*. The locations of the three probes are shown in a frontal view in FIG. 10*d*, in a side view in FIG. 10*e*, and in a bottom view in FIG. 10*f*. In this embodiment the signals from third probe 950 will be analyzed separately and this additional information will be added to the information recorded with second probe 110. While adding to the complexity and cost of the equipment and the procedure, the method is substantially increases the overall sensitivity of the screening test when performed with Tc-99m.

The additional probe 950 may require position adjustment to view proper part of the heart, e.g. left ventricle. This can be achieved by guiding the probe by ultrasound, X-ray radiation, or using additional radiation source. For example, probe positioning technique may involve injecting of small amounts of TI-201 (on the order of 50 microCurie) and then directing the probe at the LV region by maximum count rate criterion. In this case one pre-injection would be performed 5–10 minutes before the main screening test procedure.

In the case of higher energy isotopes such as I-131, or In-113m, the above addition will not be necessary. Persons of ordinary skill in the relevant art will recognize that dosage of radioisotopes used in nuclear medicine are strictly regulated, thereby restricting the practical range of available doses. Furthermore, lower doses are typically preferred over higher doses, if similar clinical results obtain from differing doses. In clinical trials of the screening system of the present invention, the results described herein have been achieved with doses of various radioisotopes emitting as little as 50 microCurie.

The purpose of the multi-probe (alternatively and interchangeably referred to herein as multi-detector, multi-sensor or multi-pixel) approach of the present invention, and particularly of the exemplary embodiment, is to assure that the measurement is performed on the left ventricular bolus transit accompanying that of the aorta. While positioning of the first (aortic) probe is relatively simple to perform for each patient, and no multiple sensors are necessary, technologists operating the system may have a problem in positioning the second ventricular probe above the heart's left ventricle. To remedy the potential mispositioning, thus collecting activity from superimposed left and right heart regions, the multi-probe system collects data from a larger region that necessarily encompasses the left ventricle.

Figure 11:
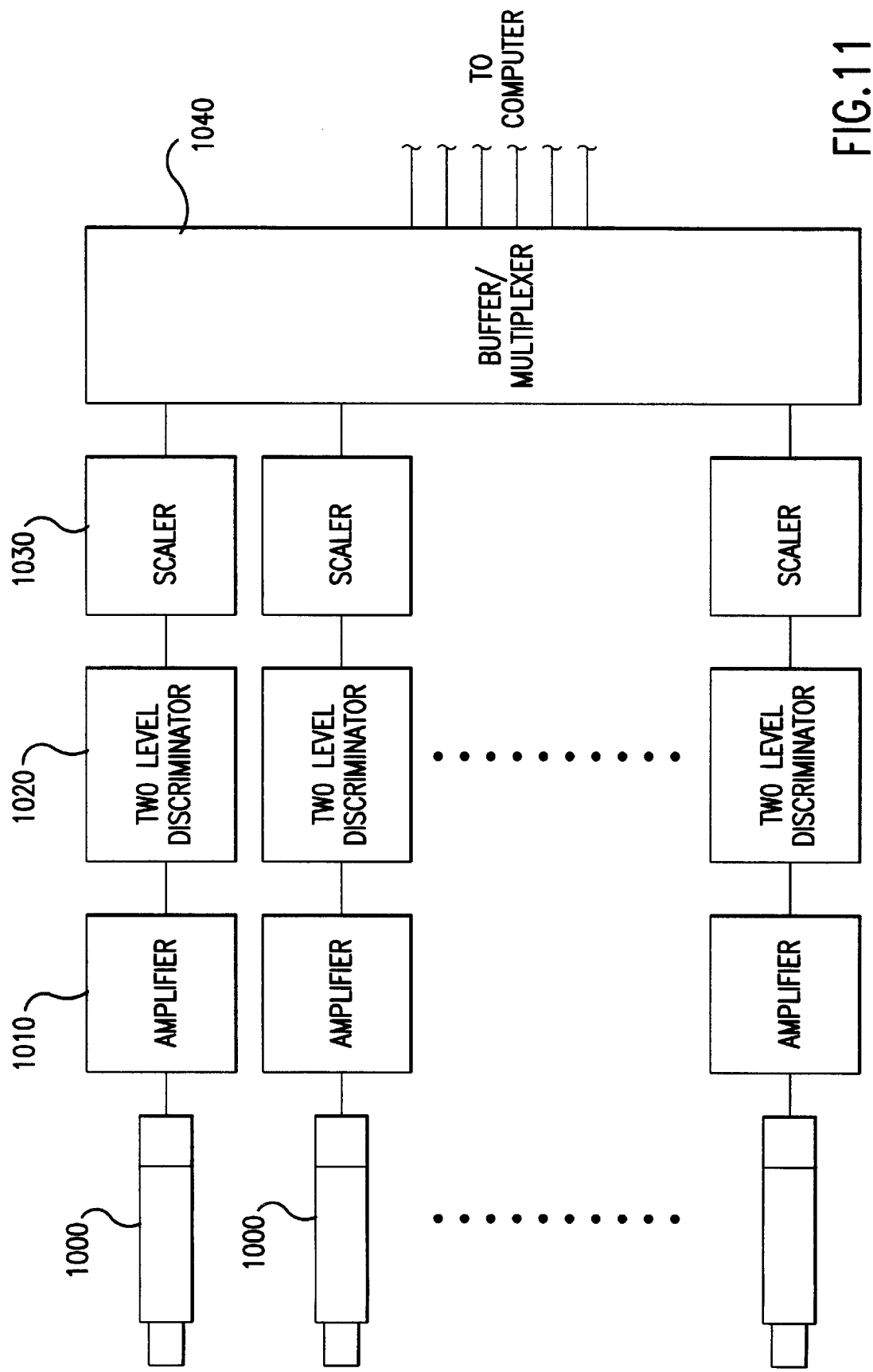
FIG. 11 is a flowchart of the data processing features of the probe from FIG. 10a and FIG. 10b of the present invention.

To achieve high rate capability necessary for the probe operation, a parallel readout of the second multi-element probe sensors can be implemented. FIG. 11 shows a schematic of a possible readout system with a multitude of fast scalers (for example sixteen in the case of the second gamma detector probe design from FIG. 10*a* and FIG. 9*b*. In this embodiment each PMT module 1000 of the PMT detector array is connected in series to a dedicated amplifier 1010, two level discriminator 1020, and scaler 1030, preferably using a single channel. After amplifying the signal, the output of amplifier 1010 is connected to a two-level discriminator 1020 (also called single-channel analyzer) which produces output pulse when the probe signal falls in the accepted amplitude range for the particular gamma energy (depending on the isotope) used. The discriminators 1020 can have individual computer-controlled settings for each employed gamma energy. The output pulses from discriminator 1020 are subsequently counted in scalers (counters) 1030 within appropriate adjusted time bins, typically from 0.1 second to 1 second. The bank of all scalers 1030 is then connected to a buffer/multiplexer 1040 to send the digitized time-binned data to the computer (not shown). As a result of the readout system depicted in FIG. 11, it is possible to record the count-rate information from each probe within the duration of the test being performed using the exemplary Non-Invasive Screening Probe System. The count rate information will be then converted into individual time activity curves, such as shown above in Graph 1 and Graph 2.

The same readout concept of FIG. 11 can be applied to the probe design of the type shown in FIG. 8 and FIG. 9. In such a case, each individual PMT 1000 of FIG. 11 will be replaced by a readout element of a multi-anode PMT array.

Second Example of a Preferred Embodiment

In some cases it would be advantageous to perform the screening test with several radiopharmaceuticals used simultaneously in the same patient. Such situations might arise when a more precise version of the screening procedure is necessary. For example, the first radiopharmaceutical can be used to "lighten" the cardiac region to enable more precise positioning of the probes for the proper dynamic part of the screening procedure. In this case the second radiopharmaceutical compound will be injected while the first compound will be still circulating in the blood stream and/or will be present in the myocardium or in other parts of the patient's heart. In another possible situation both compounds will be injected at the same time because they will have a different role to play in the screening test and their temporal distribution in the blood stream and heart tissue will be different and complementary. There might be many other situations when by injection or by other route of entering of several radiopharmaceuticals to the same patient will be necessary or beneficial to the screening test and/or to other diagnostic procedures. In some cases the additional radiopharmaceuticals can come from other than cardiac-related procedures. In all these cases it would be beneficial or even necessary to operate the screening probe system at presence of different radiations emanating from the patient.

The Tc-99m radioisotope is used in most nuclear medicine cardiac imaging studies. I-131 radioactive label would be preferred in the screening probe test. I-131 is easy to use and emits gamma radiation of higher than Tc-99m energy (360 keV vs. 140 keV) that penetrates the patient's body with less scatter and absorption on its way to the detector. Clearer picture of flow distribution is therefore obtained. Additionally, a much lower injection dose of about 200 microCurie (vs many milliCurie) will suffice to perform the screening test. However, I-131 emits also highly ionizing beta radiation and the regulations intended to minimize patient exposure to radiation limit the availability of this radiolabel. Used in the past in diagnostic imaging of kidneys, I-131 is presently not readily available. It is however possible that the advantages of the screening test will outbalance the harm effects of its radiation and it will become available again. Short lived (2 minute half-life) 0–15 positron emitter (emitting 511 keV annihilation gamma rays) used in water is a very good performing and well accepted tracer for blood flow studies. Therefore, the screening probe system of the present invention is designed to accommodate the higher energy gamma emitters in addition to the lower energy of Tl-201 (60–80 keV) and Tc-99m (140 keV). With an efficient and high count rate system a high temporal resolution is possible to improve precision of the screening test.

Figure 12:
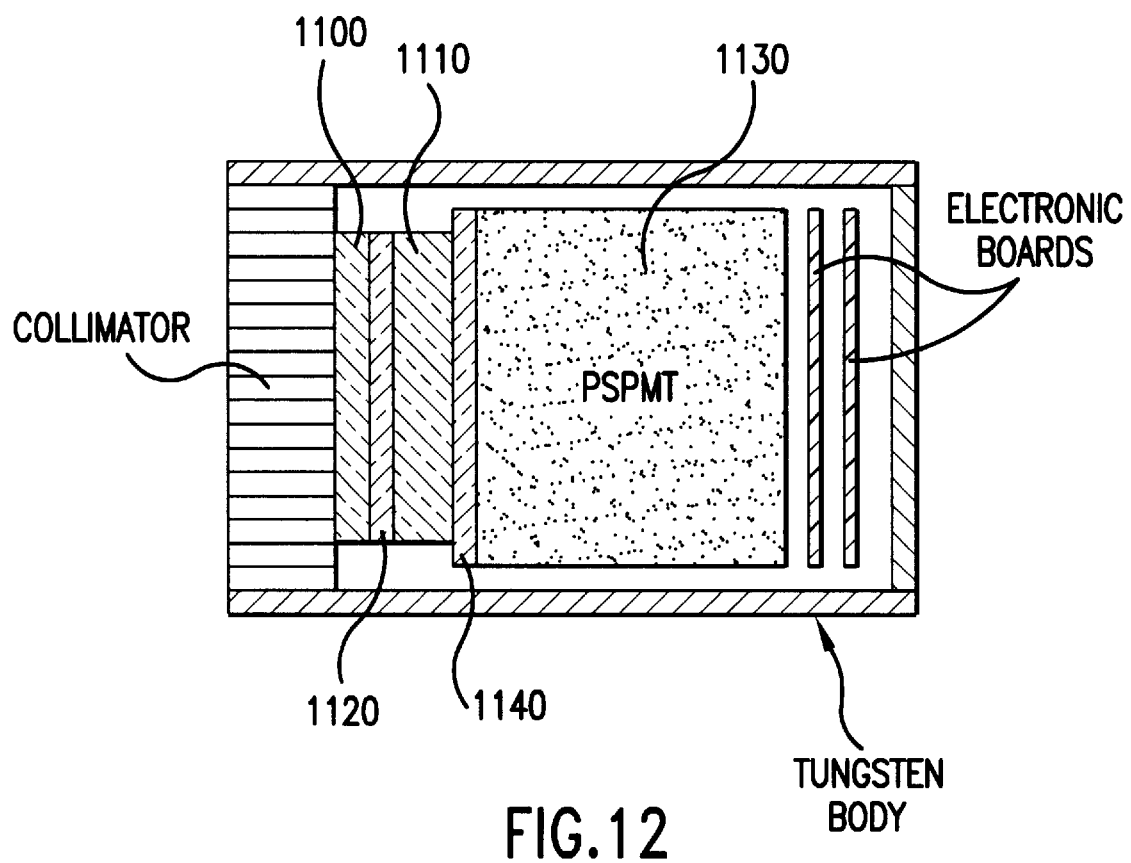
FIG. 12 is a side view cross sectional diagram of a second specific embodiment of an improved gamma detection probe.

To separate signal contributions from these compounds in the screening probe system, the mixture of applied radiopharmaceuticals will be typically composed of compounds labeled with different radionucleides. The differing radiation emissions from these radionucleides can be distinguished in the probe system of the present invention by the different characteristics of the signals accompanying detection of gamma or beta rays from these radionucleides. For example, the first compound can be labeled with Tc-99m emitting 140 keV gamma rays, while the second compound can include positron emitter such as 0–15 or F-18, which in turn will produce 511 keV annihilation gamma rays detected by the probes. To differentiate between these differing gamma radiations emitted by the different components in the radiopharmaceutical mixture, the screening system of the present invention is equipped with sufficient differentiation power. It also possesses sufficient detection efficiency of the potentially broad spectrum of gamma ray energies emitted from the different radionucleides. In a preferred embodiment, the screening system can be built with a single material, possessing both high stopping power and high energy resolution. However, in practical situations even when using the best available high energy resolution solutions such as solid state CdZnTe there will be always signal and information overlap from the two or more radiation components from the radiopharmaceutical mixture. To maximize this differentiation power a unique solution can be implemented possible only with scintillators and not with solid-state materials such as CdZnTe. In this solution two differing scintillation materials will be optically coupled to the same photodetector. An example of such an implementation is shown in FIG. 12. A preferably pixellated first scintillator layer such as NaI(T1), (CsI(T1), or CsI(Na) array 1100 of ~3×3×6 mm pixels with a ~50 mm square active coverage will be optically coupled to the second layer 1110 of a heavy scintillator such as Gadolinium Oxyorthosilicate (GSO) in the form of a square slab 1 cm thick and 6 cm on a side. Other examples of the second scintillator material are: Lutetium Oxyorthosilicate (LSO) or a Lutetium-Gadolinium Oxyorthosilicate (LGSO) which is a crystal scintillator produced as a mixture of GSO and LSO. Scintillation light from the first scintillator 1100 produced on detection of gamma rays in its material is transported via the optically transparent medium of the second scintillator 1110 to the following optional light guide (not shown) and then to the photocathode of the photomultiplier 1130 via the glass window 1140 of the photomulitplier. Optical coupling compound and additional optical window 1120 can be used between the first and second scintillation layers. For example, in the NaI(T1) scintillator case an enclosure with a transparent glass window is used to prevent corrosion of the scintillation material on contact with air and humidity. Major fraction of scintillation light produced in the second scintillator 1110 from gamma rays interacting in this scintillator 1110 enters the photomultiplier 1130 via the optional optical window (not shown) or light guide and the glass photomultiplier window 1140 finally to be stopped and converted to an electronic signal in the photocathode of the photomultiplier 1130.

The thickness of the first scintillator 1100 is selected as to efficiently detect gamma radiation up to about 150 keV while the second scintillator 1110 is intended to be optimized for higher energy gamma rays such as 360 keV from I-131, 390 keV from In-113 m or 511 keV annihilation photons from positron emitters such as 0–15 or F-18. While most of the lower energy gamma rays will be stopped in the first scintillator layer, a major fraction of the higher energy gamma rays will pass undisturbed through the first scintillator 100 and will interact and be detected in the second scintillator layer 1110.

In this described preferred embodiment, the two scintillators selected for the two scintillator layers differ not only in their gamma radiation stopping power but also in their scintillation characteristics such as light output measured in light photons per unit of energy of the absorbed radiation, and their scintillation light emission temporal characteristics. It is desirable that both scintillators have similar and high light outputs while their temporal characteristics expressed in time duration of the scintillation signal are sufficiently different so as to enable temporal analysis of the shape of each scintillation pulse to be performed by dedicated electronic signal analyzing circuitry incorporated in the probe system of the present invention. This circuitry and the proper software algorithm installed in the probe system's computer will enable differentiation of the pulses produced from lower energy gamma photons interacting in the first scintillator layer 1100 from the signals produced in the second scintillator layer 1110 which mostly originate from higher energy gamma rays.

As disclosed in this preferred embodiment, NaI(T1) and GSO constitute a very well balanced pair of two practical scintillators possessing optimal characteristics fulfilling the above discussed requirements for a proper operation of the dual-energy probe.

In this dual energy detection system embodiment of the present invention, interference between the two radiation components coming from two or more radiopharmaceuticals is minimized. Independent dynamic curves for mixture of at least two radiopharmaceuticals can be obtained. While complicating the probe design, this added analytical power of the present embodiment of the screening probe system can become of prime importance in the future due to the increasing role of multi-radiopharmaceutical nuclear medicine imaging and multi-modality diagnosis in general.

The photomultiplier solution used in this example of a preferred embodiment is a commercially available single 3" square model R2487 (or a similar model R3941) position sensitive photomultiplier (PSPMT) from Hamamatsu Photonics. Its useful photocathode size is about 2" square which is entirely adequate for the second example of a screening probe embodiment of the present invention.

In contrast to the previously discussed embodiment of the screening probe system with two different probe designs for the first (simpler, no pixellation) and the second (pixellated) probe the above design is applicable to both probes of the screening system.

The disclosed Cardiovascular Non-Invasive Screening Probe System and Method for Coronary Artery Disease procedure shows an important difference in time shapes of the activity-time curves obtained during radionucleide angiography at the left ventricular (LV) and the ascending aorta (AA) heart regions. As will be apparent to persons of ordinary skill in the relevant art, several possible criteria can be used to characterize these curve differences, and these criteria are appropriately used in data processing software. For example, the ratio of the areas under the downslopes of the two activity-time curves of Graph 1 and Graph 2 can be taken. Alternatively, the differences in the decay-time slopes (i.e., the ratio of the disappearance times) from the AA and the LV regions of Graph 3 and Graph 4 can be used. In clinical trials, even these simple criteria allowed for high sensitivity and specificity of the CAD detection.

The data collected and transmitted using the exemplary Cardiovascular Non-Invasive Screening Probe System and Method for Coronary Artery Disease is computer-analyzed to identify the left ventricular position, measure the bolus dynamic time curve and compare it to the aortic probe dynamic data. A fast criterion can be used to select the proper probe in the array corresponding to the left ventricular measurement by choosing the array sensor with the lowest initial peak (right heart contribution) in the double activity time curve shown in Graph 1. The peak value of the earlier (right heart) peak should be lower than 80% of the later peak from the left ventricle. If not properly positioned, the contribution from the superimposed right heart will steepen the descending slope of the left ventricular curve, simulating the effect of the coronary disease and this must be avoided. The comparison of the properly obtained two dynamic activity curves for the aorta and flow left ventricle may be used as a diagnostic indication of the potential diagnostic indication of the coronary occlusive disease.

Other advantages of the proposed Cardiovascular Non-Invasive Screening Probe System and Method for Coronary Artery Disease include the following:

Short duration test with little physical (and emotional) stress for the patient; Resultant limited time of patient exposure to radiation, by using materials with short biological half-lives that are purged quickly from the system, such as Tc99m-DTPA and hippuran. Typically, the Tc99m-sestamibi used in the first pass heart imaging procedure is uptaken in the heart's myocardium and stays there for a longer period of time and the half-life (6 hours) of Tc99m is defining the radiation dose to the patient; and High efficiency for relevant tracers emitting higher-energy gamma photons, such as 360 keV from 1–131 (8-day half-life, used in hippuran), 390 keV from In-113m (1½ hours half-life), and 511 keV from F-18 (2 hours half-live, used in fluorodeoxyglucose, FDG) and 0–15 (2 minute half-life) used in O15-water.

While the invention has been described and illustrated herein by references to various specific embodiments, it is understood that the invention is not restricted to those particular embodiments and descriptions selected for that purpose. It will, however, be evident to those skilled in the art that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A gamma imager, comprising:
an array of scintillators producing a scintillator output;
an array of compact position sensitive photomultiplier tubes forming a single detector head for receiving the scintillator output, the array of photomultiplier tubes producing a photomultiplier output; and
electronic circuitry for receiving the photomultiplier output; wherein, the array of scintillators, the array of photomultiplier the gamma imager with a rate capability greater than 100 kHz.

2. The imager of claim 1, wherein the array of compact position sensitive photomultiplier tubes comprises a plurality of photomultiplier tubes.

3. The imager of claim 1, wherein the array of compact position sensitive photomultiplier tubes comprises a flat photomultiplier array.

4. The gamma imager of claim 1, further comprising a collimator for restricting gamma radiation incident on the array of scintillators, the collimator having a plurality of openings about 5 mm in diameter or larger.

5. The gamma imager of claim 1, wherein the array of scintillators has an area no greater than about 25 $cm^2$.

6. The gamma imager of claim 1, wherein the array of scintillators has a pixel size from about 5 mm to about 10 mm.

7. A system comprising:
a first gamma probe; and
a second gamma probe;
wherein the first gamma probe and the second gamma probe each include:
a housing having an open end;
a collimator located at the open end of the housing;

a scintillator array located within the housing, wherein the scintillator array produces an output;

at least one photomultiplier tube module located within the housing for receiving the scintillator array output; and electronic circuitry coupled to the at least one photomultiplier tube module;

wherein, with reference to a patient lying on his back, the first gamma probe can be placed against the patient's body over the patient'chest wall over the aorta in a vertical left-to-right plane perpendicular to horizontal side-to-side plane;

and the second gamma probe can be simultaneously placed against the patient's body and tilted 30 degrees toward the patient's left side in a vertical side-to-side plane and 10 degrees toward the patient's feet in a head-to-toe plane relative to the first gamma probe.

8. The system of claim 7, further comprising:

a support gantry/harness for supporting the first gamma probe and the second gamma probe, wherein the support gantry/harness provides co-registration of the first gamma probe and the second gamma probe.

9. The system of claim 7, further comprising:

control electronics for controlling the first gamma probe and the second gamma probe;

an analog-to-digital converter coupled to the first gamma probe and the second gamma probe;

a memory module coupled to the analog-to-digital converter; and a central processing unit coupled to the memory module.

10. The system of claim 9, wherein the central processing unit processes a first set of heart information received from the first gamma probe and a second set of heart information received from the second gamma probe using at least one algorithm.

11. The system of claim 10, further comprising:

a third gamma probe, wherein the third gamma probe receives a third set of heart information;

wherein the third gamma probe is coupled to the analog-to-digital converter;

wherein the central processing unit processes the third set of received heart information in parallel with the processing of the first set of received heart information and the second set of received heart information; and wherein the third gamma probe includes:

a housing having an open end;

a collimator located at the open end of the housing;

a scintillator array located within the housing, the collimator being located between the scintillator array and the open end of the housing, wherein the scintillator array produces an output;

at least one photomultiplier tube module located within the housing for receiving the scintillator array output; and electronic circuitry coupled to the at least one photomultiplier tube module.

12. The system of claim 7 wherein the two probes are mounted on a gantry.

13. The system of claim 7 wherein the photomultiplier tube for at least one of the probes is a compact position sensitive photomultiplier tube.

14. The system of claim 7 wherein the photomultiplier tubes are compact position sensitive photomultiplier tubes.

15. The system of claim 7, wherein the probes both have a rate capability greater than about 100 kHz.

16. The system of claim 7 wherein the scintillator array for one of the probes has an area no greater than about 25 $cm^2$.

17. The system of claim 7 wherein the system is adopted to perform a screening procedure based on coronary transit time measurements.

18. The system of claim 7 wherein the scintillator array for one of the probes has a pixel size from about 3 mm to about 20 mm.

19. The system of claim 7 wherein the collimator for one of the probes has opening about 5 mm in diameter or larger.

20. The system of claim 7 wherein the collimator for one of the probes has a single bore.

21. A gamma imager, comprising:

an array of scintillators producing a scintillator output;

an array of compact position sensitive photomultiplier tubes forming a single detector head for receiving the scintillator output, the array of photomultiplier tubes producing a photomultiplier output;

electronic circuitry for receiving the photomultiplier output; and a collimator for restricting gamma radiation incident on the array of scintillators;

wherein the collimator has a plurality of openings about 5 mm in diameter or larger.

22. The gamma imager of claim 21, wherein the array of scintillators has an area no greater than about 25 $cm^2$.

23. The gamma imager of claim 21, wherein the array of scintillators has a pixel size from about 5 mm to about 10 mm.

24. A system comprising:

a first gamma probe; and a second gamma probe;

wherein the first gamma probe and the second gamma probe each include:

a housing having an open end;

a collimator located at the open end of the housing;

a scintillator array located within the housing, wherein the scintillator array produces an output;

at least one photomultiplier tube module located within the housing for receiving the scintillator array output; and electronic circuitry coupled to the at least one photomultiplier tube module;

wherein the two probes can be directed at a single target with the direction from the first probe to the target at a right angle to the direction from the second probe to the target, the locations of the target and the two probes providing three points that define a plane; and while one probe remains in fixed position, the other probe can be moved out of the plane while remaining directed at the target.

25. The system of claim 24 wherein the two probes are mounted on a gantry.

26. The system of claim 24 wherein the photomultiplier tube for at least one of the probes is a compact position sensitive photomultiplier tube.

27. The system of claim 24 wherein the photomultiplier tubes are compact position sensitive photomultiplier tubes.

28. The system of claim 24 wherein the probes both have a rate capability greater than about 100 kHz.

29. The system of claim 24 wherein the scintillator array for one of the probes has an area no greater than about 25 $cm^2$.

30. The system of claim 24 wherein the system is dedicated to a screening procedure based on coronary transit time measurements.

31. The system of claim 24 wherein the scintillator array for one of the probes has a pixel size from about 3 mm to about 20 mm.

32. The system of claim 24 wherein the collimator for one of the probes has opening about 5 mm in diameter or larger.

33. The system of claim 24 wherein the collimator for one of the probes has a single bore.

34. A gamma imager, comprising:
   an array of scintillators producing a scintillator output;
   an array of compact position sensitive photomultiplier tubes forming a single detector head for receiving the scintillator output, the array of photomultiplier tubes producing a photomultiplier output; and
   electronic circuitry for receiving the photomultiplier output; wherein the gamma imager is of a size whereby two of the gamma imagers, a first and a second, can be placed simultaneously as follows:
   with reference to a patient lying on his back, the first gamma imager against the patient's body over the patient's chest wall over the aorta in a vertical left-to-right plane perpendicular to the horizontal side-to-side plane;
   and the second gamma imager placed against the patient's body and tilted 30 degrees toward the patient's left side in a vertical side-to-side plane and 10 degrees toward the patient's feet in a head-to-toe plane relative to the first gamma imager.

* * * * *